United States Patent [19]
Petersen et al.

[11] 4,234,572
[45] Nov. 18, 1980

[54] 1-N-4,6-DI-O-(AMINOGLYCOSYL)-1,3-DIAMINO-CYCLITOL DERIVATIVES, PROCESSES FOR THEIR PREPARATION AND THEIR USE

[75] Inventors: Uwe Petersen, Leverkusen; Eckart Voss, Cologne; Karl G. Metzger, Wuppertal; Peter Stadler, Haan, all of Fed. Rep. of Germany

[73] Assignee: Bayer Aktiengesellschaft, Leverkusen, Fed. Rep. of Germany

[21] Appl. No.: 960,205

[22] Filed: Nov. 13, 1978

[30] Foreign Application Priority Data

Dec. 2, 1977 [DE] Fed. Rep. of Germany ....... 2753769

[51] Int. Cl.$^3$ ...................... A61K 31/71; C07H 15/22
[52] U.S. Cl. ..................................... 424/180; 536/10; 536/17 R

[58] Field of Search ................ 424/180; 536/17, 17 R

[56] References Cited

U.S. PATENT DOCUMENTS

| | | | |
|---|---|---|---|
| 4,053,591 | 10/1977 | Daniels et al. | 536/17 |
| 4,062,947 | 12/1977 | Wright et al. | 536/17 |
| 4,086,415 | 4/1978 | Suami et al. | 536/17 |

*Primary Examiner*—Johnnie R. Brown
*Attorney, Agent, or Firm*—Sprung, Felfe, Horn, Lynch & Kramer

[57] ABSTRACT

The invention relates to 1-N-4,6-di-O-(aminoglycosyl)-1,3-diamino-cyclitol derivatives useful as antimicrobial agents. Also included in the invention are methods for preparing said derivatives, the provision of pharmaceutical compositions containing said derivatives and methods for the use of said derivatives and compositions.

23 Claims, No Drawings

1-N-4,6-DI-O-(AMINOGLYCOSYL)-1,3-DIAMINO-CYCLITOL DERIVATIVES, PROCESSES FOR THEIR PREPARATION AND THEIR USE

The present invention relates to 1-N-4,6-di-O-(aminoglycosyl)-1,3-diamino-cyclitol derivatives, processes for their preparation and their use as medicaments, in particular as antimicrobial agents.

Aminoglycoside antibiotics are important substances for effectively combating bacterial infections. However, the appearance of resistant germs reduces their broad applicability in many cases; furthermore, side-effects can occur. In some cases it may be desirable to avoid these disadvantages by using derivatives of aminoglycoside antibiotics.

Examples which are already known of such derivatives of aminoglycose antibiotics are 1-N-(4-amino-2-hydroxy-butyryl)-kanamicin A, 1-N-acetylsisomicin and 1-N-ethyl-sisomicin (DT-OS (German Published Specification) No. 2,437,160).

According to the present invention there is provided a compound of the general formula

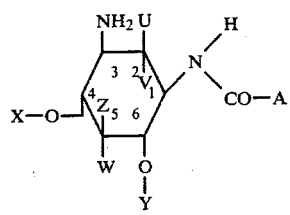

or a salt thereof, in which
X denotes a radical of the formula

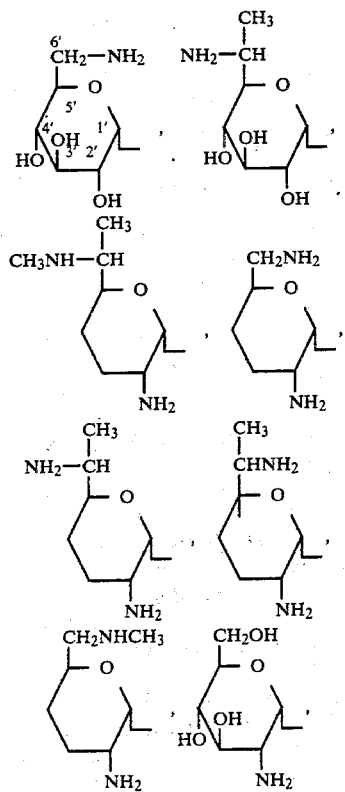

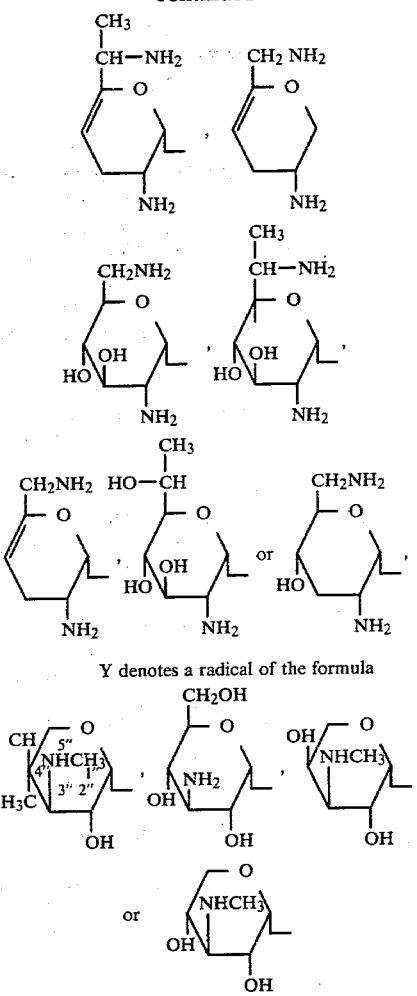

Y denotes a radical of the formula

U, V, and W independently denote a hydrogen atom or a hydroxyl group, but U and V cannot be OH simultaneously, Z denotes a hydrogen atom or a hydroxyl or amino group, and
A denotes a radical

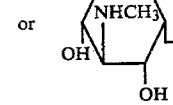

in which
R denotes an alkyl, alkenyl, alkinyl, cycloalkyl, aryl, aralkyl, heterocyclyl or heterocyclylalkyl group it being possible for the radicals R mentioned to be substituted:
$R^1$, independently of R, has any of the meanings indicated for R or denotes a hydrogen atom; and
$R^2$, independently of $R^1$ has any of the meanings given for $R^1$, or denotes a hydroxyl, alkoxy, cycloalkoxy, optionally substituted aralkoxy, heterocyclyloxy, amino, alkylamino, dialkylamino or alkoxycarbonyl group or a group of the general formula

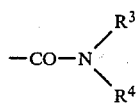

in which
R³ and R⁴ independently denote any of the meanings given for R¹ or denote a hydroxyl, alkoxy, cycloalkoxy, optionally substituted aralkoxy, heterocyclyloxy, hydroxyl, amino, alkylamino or dialkylamino group, or R¹ and R² or R³ and R⁴, including the N atom to which they are bonded, form a saturated heterocyclic ring.

These compounds and their pharmaceuticaly acceptable salts exhibit powerful antibacterial properties against a number of germs and are particularly well tolerated.

The pharmaceutically acceptable salts are derived from inorganic or organic acids, such as, sulphuric acid, phosphoric acid, nitric acid, hydrochloric acid, hydrobromic acid, acetic acid, propionic acid, ascorbic acid and citric acid.

The 1-N-4,6-di-O-(aminoglycosyl)-1,3-diaminocyclitol derivatives according to the invention, of the formula I, which are derived from an antibiotic selected from gentamicin A, gentamicin B, gentamicin B₁, gentamicin C₁, gentamicin C₁ₐ, gentamicin C₂, gentamicin C₂ₐ, gentamicin C₂ᵦ, gentamicin X₂, sisomicin, verdamicin, tobramicin, G-418, 66-40B, 66-40D, JI-20A, JI-20B, G 52, mutamicin 1, mutamicin 2, mutamicin 4, mutamicin 5 and mutamicin 6, and which carry the radical —CO—A on the 1-N atom of these antibiotics, are of particular interest.

Of these, the 1-N-sisomicin derivatives represented by formula II

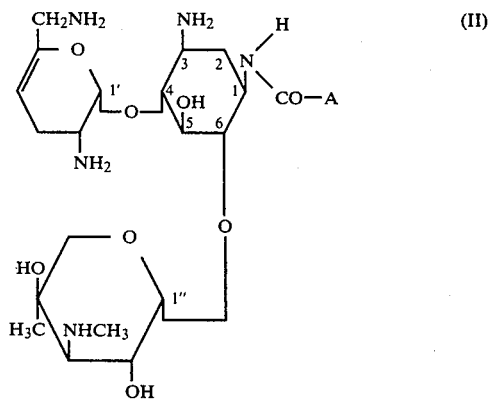

are particularly valuable.

Alkyl in the definitions of R, R¹, R², R³ and R⁴ is straight-chain or branched alkyl with preferably 1 to 10, in particular 1 to 5, carbon atoms. Examples which may be mentioned are methyl, ethyl, n- and iso-propyl, n-, iso- and tert.-butyl and decyl.

Alkenyl in the definititons of R, R¹, R², R³ and R⁴ is straight-chain or branched alkenyl with preferably 3 to 6 carbon atoms. Examples which may be mentioned are: allyl, isobutenyl and dimethylallyl.

Alkinyl in the definitions of R, R¹, R², R³ and R⁴ is straight-chain or branched alkinyl with preferably 3 to 6, in particular 3 or 4, carbon atoms. An example which may be mentioned is propargyl.

Cycloalkyl in the definitions of R, R¹, R², R³ and R⁴ is monocyclic, bicyclic or tricyclic cycloalkyl with preferably 3 to 10, in particular 3 to 7, carbon atoms. Examples which may be mentioned are cyclopropyl, cyclobutyl, cyclopentyl, cyclohexyl, cycloheptyl, bicyclo[2,2,1]-heptyl, bicyclo[2,2,2]octyl and adamantyl.

Aryl in the definitions of R, R¹, R², R³ and R⁴ is aryl preferably mono- or bi-cyclic carbocyclic aryl, with preferably 6 or 10 carbon atoms in the aryl part. Examples which may be mentioned are phenyl or naphthyl.

Aralkyl in the definitions of R, R¹, R², R³ and R⁴ is aralkyl with preferably 6 or 10, in particular 6, carbon atoms in the aryl part, which is preferably mono- or bi-cyclic carbocyclic aryl and preferably 1 to 4, in particular 1 or 2, carbon atoms in the alkyl part, it being possible for the alkyl part to be straight-chain or branched. Examples which may be mentioned are benzyl and phenylethyl.

Heterocyclyl in the definitions of R, R¹, R², R³ and R⁴ is a hetero-paraffinic, hetero-aromatic or heteroolefinic 5-membered to 7-membered, preferably 5-membered or 6-membered, ring with preferably 1 to 3, in particular 1 or 2, identical or different hetero-atoms. Hetero-atoms are oxygen, sulphur or nitrogen. Examples which may be mentioned are pyrrolidinyl, piperidinyl, tetrahydrofuryl, tetrahydropyranyl, piperazinyl, morpholinyl, furyl, thienyl, pyrazolyl, pyridyl, pyrimidinyl, pyrrolyl and 1,2,3- and 1,2,4-triazolyl.

Heterocyclylalkyl in the definitions of R, R¹, R², R³ and R⁴ is heterocyclylalkyl in which the heterocyclyl radical has the meanings indicated above and the alkyl part preferably contains 1 to 6, in particular 1 to 4, carbon atoms. Examples which may be mentioned are: tetrahydrofurylmethyl, tetrahydropyranylmethyl, 1,3-dioxolanylmethyl, 1,3-dioxolanyl-β-ethyl, 1,3-dioxolanyl-γ-propyl, 1,3-dioxolanyl-δ-butyl, 1,3-oxathiolanylmethyl 1,3-dithiolanylmethyl, furfuryl, thienyl, pyridylmethyl and 1,4-dioxaspiro[4,5]decan-2-yl-methyl.

If R¹ and R², and/or R³ and R⁴, together with the amide nitrogen atom, form a saturated heterocyclic ring, this heterocyclic ring can contain, as further hetero-atoms, 1 to 3, preferably 1, oxygen, sulphur or nitrogen atom, and as hetero-groups, preferably a SO₂ group or N-alkyl group, alkyl in the N-alkyl group preferably containing 1 to 4, in particular 1 or 2, carbon atoms. Alkyl which may be mentioned are methyl, ethyl, n- and iso-propyl and n-, iso- and tert.-butyl. The heterocyclic ring contains 5 to 7, preferably 5 or 6, ring members. The 6-membered heterocyclic ring preferably contains the hetero-atom or the hetero-group in the para-position relative to the amide nitrogen atom. Examples which may be mentioned of the heterocyclic ring are pyrrolidine, piperidine, piperazine, hexamethyleneimine, morpholine, N-methylpiperazine, isoxazolidine and tetrahydroisoxazine.

Alkoxy in the definitions of R², R³ and R⁴ preferably contains 1 to 6, in particular 1 to 4, carbon atoms in the alkyl radical. Examples which may be mentioned are methoxy and ethoxy. Cycloalkoxy in the definitions of R², R³ and R⁴ preferably designates a cycloalkoxy radical with 3 to 10, in particular 3 to 7, carbon atoms. Examples which may be mentioned are cyclopentyloxy and cyclohexyloxy.

Heterocyclyloxy in the definitions of R², R³ and R⁴ is derived from hetero-paraffinic, hetero-aromatic or hetero-olefinic 5-membered to 7-membered, preferably 5- membered or 6-membered, rings with preferably 1 to 3, in particular 1 or 2, identical or different hetero-atoms. Hetero-atoms are oxygen, sulphur or nitrogen. Examples which may be mentioned are tetrahydropyranyloxy and tetrahydrofuranyloxy.

Aralkoxy in the definitions of $R^2$, $R^3$ and $R^4$ is preferably phenylalkoxy with preferably 1 to 4, in particular 1, carbon atoms in the alkyl part. An example which may be mentioned is benzyloxy.

Alkylamino and dialkylamino in the definition of $R^2$, $R^3$ and $R^4$ preferably contain 1 to 6, in particular 1 to 4, carbon atoms in the alkyl radical. Examples which may be mentioned are methylamino and dimethylamino.

Alkoxycarbonyl in the definition of $R^2$ preferably contains 1 to 6, in particular 1 to 4, carbon atoms in the alkyl radical. Examples which may be mentioned are: methoxycarbonyl and ethoxycarbonyl.

The abovementioned alkyl, alkenyl, alkinyl, cycloalkyl, aryl, aralkyl, heterocyclyl and heterocyclylalkyl radicals can be substituted by one or more identical or different radicals. They preferably contain 1 to 3, in particular 1 or 2, substituents, of which there may be mentioned, as examples: halogen, preferably chlorine or bromine, cyano, hydroxyl, mercapto, alkyl and alkoxy with preferably 1 to 6, in particular 1 to 4, carbon atoms, for example methyl and ethyl, and methoxy and ethoxy, alkenyloxy with preferably 3 to 6, in particular 3, carbon atoms, for example allyloxy, phenoxy, carboxyl, carbamido, alkoxycarbonyl with preferably 1 to 6, in particular 1 to 4, carbon atoms in the alkyl part, which in turn can be substituted by hydroxyl, alkoxy or amino, such as ethoxycarbonyl, cycloalkyl with 3 to 6 carbon atoms, for example cyclopropyl or cyclohexyl, amino, alkylamino and dialkylamino with preferably 1 to 6, in particular 1 to 4, carbon atoms per alkyl group, which can be further substituted by hydroxyl, alkoxy or amino, and trifluoromethyl.

The compounds of the formula I in which
A denotes a radical —OR or

wherein
R denotes an alkyl radical with 1 to 10, in particular 1 to 6, carbon atoms, which optionally carries 1 or 2 substituents selected from halogen, preferably chlorine; hydroxyl; mercapto; cyano and carboxyl; trifluoromethyl; alkoxy and alkylthio with 1 to 6 carbon atoms in each case, in particular methoxy and ethoxy, which can be substituted in the alkyl part by amino or monoalkylamino and dialkylamino with 1 to 4 C atoms per alkyl group in each case, and allyloxy; phenoxy; and a radical of the general formula

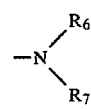

in which
$R_6$ denotes a hydrogen atom or a $C_1$ to $C_8$ alkyl or allyl and $R_7$ denotes a hydrogen atom or a $C_1$ to $C_8$ alkyl, $C_5$ to $C_7$ cycloalkyl, $C_5$ to $C_7$ cycloalkyl-$C_1$ to $C_4$ alkyl, phenyl, phenyl-$C_1$ to $C_4$ alkyl or allyl group, and in which
the alkyl, cycloalkyl and phenyl radicals $R_6$ and $R_7$ are optionally substituted by one or two substituents selected from alkoxy with 1 to 4 carbon atoms, amino, monoalkylamino and dialkylamino with 1 to 4 carbon atoms per alkyl group in each case and hydroxyl, alkoxycarbonyl with 1 to 4 carbon atoms in the alkyl radical and cycloalkyl with 3 to 6 carbon atoms in the ring; or R denotes an alkenyl radical with 3 to 7 carbon atoms, preferably allyl; or denotes an alkinyl radical with 3 or 4 carbon atoms, preferably propargyl; or denotes a monocyclic or bicyclic cycloalkyl radical with 3 to 7 carbon atoms, which can contain 1, 2 or 3 substituents selected from alkyl with 1 to 4 carbon atoms, in particular methyl and ethyl, alkoxy with 1 to 4 carbon atoms, in particular methoxy and ethoxy, hydroxyl, amino and alkylamino and dialkylamino with 1 to 4 carbon atoms per alkyl group, in particular methylamino and dimethylamino; or denotes a phenyl radical or benzyl radical, which is optionally substituted by nitro, halogen, preferably chlorine, or alkoxy with 1 to 4 carbon atoms; or denotes a piperidinyl, tetrahydropyranyl, tetrahydrofuryl, 1,3-dioxolanyl or 1,3-dioxolano[d,b-]tetrahydrofuryl radical, which is optionally substituted by 1 or 2 radicals selected from alkoxy with 1 to 4 carbon atoms, preferably methoxy and ethoxy, hydroxyl, alkyl with 1 to 4 carbon atoms, in particular methyl and ethyl, and 2,2-dimethyl-1,3-dioxolan-4-yl; or denotes a 1,3-dioxolanylalkyl, tetrahydrofurylalkyl, tetrahydropyranylalkyl, oxetanylalkyl, 1,3-oxathiolanylalkyl, 1,3-dithiolanylalkyl, 1,4-dioxaspiro[4,5]-decanyl, oxiranylalkyl, piperidinylalkyl, tetrahydropyridinylalkyl or aziridinylalkyl radical in which the alkyl radical contains 1 to 4, preferably 1 or 2, carbon atoms and which can carry 1 or 2 substituents selected from alkyl with 1 to 4 carbon atoms, preferably methyl and ethyl, phenyl and alkoxy with 1 to 4 carbon atoms, preferably methoxy and ethoxy; and $R^1$ denotes a hydrogen atom, an alkyl group with 1 to 4 carbon atoms, which can be substituted by hydroxyl or cyano, or an allyl group and $R^2$ independently of R has any of the meanings given above for R or denotes a hydrogen atom or a 1-β-tetra-O-acetyl-D-glucosyl, 1-β-D-glucosyl, tetrahydropyridinyl, morpholino, piperidino, alkoxy with 1 to 4 carbon atoms, cyclopentyloxy, cyclohexyloxy, benzyloxy which is optionally substituted by halogen, preferably chlorine, tetrahydropyranyloxy, tetrahydrofuranyloxy, hydroxyl, amino, alkylamino and dialkylamino with 1 to 4 carbon atoms per alkyl group, preferably methyl- and ethylamino, alkoxycarbonyl with 1 to 4 carbon atoms in the alkyl radical, preferably methoxycarbonyl and ethoxycarbonyl or allyloxycarbonyl group or a group of the general formula

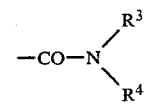

in which
$R^3$ independently of $R^1$ has any of the meanings given for $R^1$ and $R^4$ denotes a hydrogen atom, an alkyl radical with 1 to 10, in particular 1 to 6, carbon atoms which can carry 1 or 2 substituents selected from halogen, preferably chlorine, hydroxyl, mercapto, cyano, trifluoromethyl, alkoxy with 1 to 6 carbon atoms, in particular methoxy and ethoxy, allyloxy, phenoxy, amino, alkylamino and dialkylamino with 1 to 4 carbon atoms per alkyl group, in particular methylamino and dimethylamino, it being possible for the alkylamino groups mentioned to be substituted by —OH, alkoxycarbonyl with 1 to 4 carbon atoms in the alkyl radical and cycloalkyl with 3 to 6 carbon atoms in the ring, preferably cycloalkylmethyl and cycloalkylethyl; or denotes a monocyclic or bicyclic cycloalkyl radical with 3 to 7 carbon atoms, which can contain 1, 2 or 3 substituents from the group comprising alkyl with 1 to 4 carbon atoms, in particular methyl and ethyl, alkoxy with 1 to 4 carbon atoms, in particular methoxy and ethoxy, hydroxyl, amino and alkylamino and dialkylamino with 1 to 4 carbon atoms per alkyl group, in particular methylamino and dimethylamino; or denotes a hydroxyl, alkoxy with 1 to 4 carbon atoms, in particular methoxy and ethoxy or amino group or an alkylamino and dialkylamino group with 1 to 4 carbon atoms per alkyl group, in particular methyl- and ethylamino, or $R^1$ and $R^2$ or $R^3$ and $R^4$, including the N atom to which they are bonded, form a pyrrolidino, piperidino, morpholino, piperazin-4-yl, hexamethyleneimino, isoxazolin-2-yl or tetrahydroisoxazin-2-yl ring, which can carry 1 to 2 alkyl groups with 1 to 4 carbon atoms, which can be substituted by hydroxyl, are of particular interest within the scope of this invention.

In detail, new active compounds which may be mentioned are: 1-N-methoxycarbonyl-sisomicin, 1-N-ethoxycarbonyl-sisomicin, 1-N-propoxycarbonyl-sisomicin, 1-N-isopropoxycarbonylsisomicin, 1-N-butoxycarbonyl-sisomicin, 1-N-sec.-butoxycarbonyl-sisomicin, 1-N-tert.-butyoxycarbonylsisomicin, 1-N-isobutoxycarbonylsisomicin, 1-N-pentyloxycarbonyl-sisomicin, 1-N-(2,2-dimethylpropoxycarbonyl)-sisomicin, 1-N-(3-methylbutoxycarbonyl)-sisomicin, 1-N-decyloxycabonyl-sisomicin, 1-N-(2-chloroethoxycarbonyl)-sisomicin, 1-N-(b 4-chlorobutoxycarbonyl)-sisomicin, 1-N-(2-methoxyethoxycarbonyl)-sisomicin, 1-N-(2,3-dimethoxy-propoxycarbonyl)-sisomicin, 1-N-(2-hydroxyethoxycarbonyl)-sisomicin, 1-N-(2,2-dimethoxyethoxycarbonyl)-sisomicin, 1-N-(2-dimethylaminoethoxycarbonyl)-sisomicin, 1-N-(2-cyclopentyloxycarbonyl)-sisomicin, 1-N-(2-cyclohexyloxycarbonyl)-sisomicin, 1-N-(cyclopropylmethoxycarbonyl)-sisomicin, 1-N-(benzyloxycarbonyl)-sisomicin, 1-N-(allyloxycarbonyl)-sisomicin, 1-N-(propargyloxycarbonyl)-sisomicin, 1-N-(2-phenoxyethoxycarbonyl)-sisomicin, 1-N-(2,2-dimethyl-1,3-dioxolan-4-yl-methoxycarbonyl)-sisomicin, 1-N-(tetrahydrofuryl-2-methoxycarbonyl)-sisomicin, 1-N-(phenoxycarbonyl)-sisomicin, 1-N-(4-nitrophenoxycarbonyl)-sisomicin, 1-N-(1,2,5,6-di-O-isopropylidene-α-D-glucofuranosyl-3-carbonyl)-sisomicin, 1-N-(2,3-dihydroxypropoxycarbonyl)-sisomicin, 1-N-(1,3-dihydroxy-2-propoxycarbonyl)-sisomicin, 1-N-(3,4-dihydroxybutoxycarbonyl)-sisomicin, 1-N-(4,5-dihydroxypentyloxycarbonyl)-sisomicin, 1-N-(5,6-dihydroxyhexyloxycarbonyl)-sisomicin, 1-N-(2-amino-3-hydroxy-propoxycarbonyl)-sisomicin, 1-N-(3-amino-2-hydroxy-propoxycarbonyl)-sisomicin, 1-N-(2,3-diaminopropoxycarbonyl)-sisomicin, 1-N-(1,3-diamino-2-propoxycarbonyl)-sisomicin, 1-N-(2-hydroxy-3-mercapto-propoxycarbonyl)-sisomicin, 1-N-(2,3-dimercaptopropoxycarbonyl)-sisomicin, 1-N-(2-amino-ethoxycarbonyl)-sisomicin, 1-N-(2-amino-2-methyl-ethoxycarbonyl)-sisomicin, 1-N-(3-amino-propoxycarbonyl)-sisomicin, 1-N-(2-methylaminoethoxycarbonyl)-sisomicin, 1-N-(1,3-dioxolan-2-on-4-yl-methoxycarbonyl)-sisomicin, 1-N-(2-methyl-1,3-dioxolan-4-yl-methoxycarbonyl)-sisomicin, 1-N-(2-phenyl-1,3-dioxolan-4-yl methoxycarbonyl)-sisomicin, 1-N-(2,2-diethyl-1,3-dioxolan-4-yl-methoxycarbonyl)-sisomicin, 1-N-(1,4-dioxaspiro[4,5]decan-2-yl-methoxycarbonyl)-sisomicin, 1-N-(2,2-dimethyl-1,3-dioxolan-4-yl-2-ethoxycarbonyl)-sisomicin, 1-N-(2,2-dimethyl-1,3-dioxolan-4 -yl-3-propoxycarbonyl)-sisomicin, 1-N-(2,2-dimethyl-1,3-dioxolan-4-yl-4-butoxycarbonyl)-sisomicin, 1-N-(2,2-dimethyl-1,3-oxathiolan-4-yl-methoxycarbonyl)-sisomicin, 1-N-(2,2-dimethyl-1,3-dithiolan-4-yl-methoxycarbonyl)-sisomicin, 1-N-(2-tetrahydropyranylmethoxycarbonyl)-sisomicin, 1-N-(2-methoxy-tetrahydropyran-3-yl-oxycarbonyl)-sisomicin, 1-N-(2-methoxy-tetrahydrofuran-3-yl-oxycarbonyl)-sisomicin, 1-N-(2,5-dimethoxy-tetrahydrofuran-3-yl-oxycarbonyl)-sisomicin, 1-N-(oxiran-2-yl-methoxycarbonyl)-sisomicin, 1-N-(2-ethyl-oxetan-2-yl-methoxycarbonyl)-sisomicin, 1-N-(2-methoxycyclohexyloxycarbonyl)-sisomicin, 1-N-carbamoyl-sisomicin, 1-N-(methylcarbamoyl)-sisomicin, 1-N-(dimethylcarbamoyl)-sisomicin, 1-N-(ethylcarbamoyl)-sisomicin, 1-N-(N-ethyl-N-methylcarbamoyl)-sisomicin, 1-N-(propylcarbamoyl)-sisomicin, 1-N-(methyl-N-propylcarbamoyl)-sisomicin, 1-N-(isopropylcarbamoyl)-sisomicin, 1-N-(dipropylcarbamoyl)-sisomicin, 1-N-(butylcarbamoyl)-sisomicin, 1-N-(tert.-butylcarbamoyl)-sisomicin, 1-N-(isobutylcarbamoyl)-sisomicin, 1-N-(sec.-butylcarbamoyl)-sisomicin, 1-N-(pentylcarbamoyl)-sisomicin, 1-N-(tert.-pentylcarbamoyl)-sisomicin, 1-N-(hexylcarbamoyl)-sisomicin, 1-N-(2-ethylhexylcarbamoyl)-sisomicin, 1-N-(decylcarbamoyl)-sisomicin, 1-N-(methoxymethylcarbamoyl)-sisomicin, 1-N-(ethoxymethylcarbamoyl)-sisomicin, 1-N-(propoxymethylcarbamoyl)-sisomicin, 1-N-(hexyloxymethylcarbamoyl)-sisomicin, 1-N-(2-methoxyethylcarbamoyl)-sisomicin, 1-N-(2-chloroethylcarbamoyl)-sisomicin, 1-N-(cyclohexylcarbamoyl)-sisomicin, 1-N-(phenylcarbamoyl)-sisomicin, 1-N-(4-methoxyphenylcarbamoyl)-sisomicin, 1-N-(methoxycarbonylcarbamoyl)-sisomicin, 1-N-(ethoxycarbonylcarbamoyl)-sisomicin, 1-N-(phenoxycarbonylcarbamoyl)-sisomicin, 1-N-(ethoxycarbonylmethylcarbamoyl)-sisomicin, 1-N-(1-β-D-tetra-O-acetylglucosylcarbamoyl)-sisomicin, 1-N-(1-β-D-glucosylcarbamoyl)-sisomicin, 1-N-(2-hydroxyethyl-methyl-carbamoyl)-sisomicin, 1-N-(2-hydroxypropyl-carbamoyl)-sisomicin, 1-N-(bis-[2-hydroxypropyl]-carbamoyl)-sisomicin, 1-N-(3-hydroxybutylcarbamoyl)-sisomicin, 1-N-(1,1-dimethyl-2-hydroxy-ethylcarbamoyl)-sisomicin, 1-N-(1,1-bis-[hydroxymethyl]-ethylcarbamoyl)sisomicin, 1-N-(1,1-bis[hydroxymethyl]-2-hydroxyethyl-carbamoyl)-sisomicin, 1-N-(allyl-carbamoyl)-sisomicin, 1-N-(diallyl-carbamoyl)-sisomicin, 1-N-(propargyl-carbamoyl)-sisomicin, 1-N-(2,2-dimethoxyethyl-carbamoyl)-sisomicin, 1-N-(2-hydroxy-3-allyloxy-propyl-carbamoyl)-sisomicin, 1-N-(carbamidomethyl-methyl-carbamoyl)-sisomicin, 1-N-(2-dimethylaminoethylcarbamoyl)-sisomicin, 1-N-(2-diethylaminoethyl-carbamoyl)-sisomicin, 1-N-(3-dimethylaminopropyl-carbamoyl)-sisomicin, 1-N-(3-diethylaminopropyl-carbamoyl)-sisomicin, 1-N-(1-ethoxycarbonylethyl-carbamoyl)- sisomicin, 1-N-(N-cyclohexyl-N-methyl-carbamoyl)-sisomicin, 1-N-(N-cyclohexyl-N-[2-hydroxyethyl]-carbamoyl)-sisomicin, 1-N-(N-cyclohexyl-N-[2-hydroxypropyl]-carbamoyl)sisomicin, 1-N-(cyclohexylmethyl-carbamoyl)-sisomicin, 1-N-(pyrrolidinocarbonyl)-sisomicin, 1-N-(piperidino-carbonyl)-sisomicin, 1-N-(morpholino-carbonyl)-sisomicin, 1-N-(1-methyl-4-piperazinyl-carbonyl)-sisomicin, 1-N-(1-[2-hydroxyethyl]-4-piperazinyl-carbonyl)-sisomicin, 1-N-(1-hexamethyleneimino-carbonyl)-sisomicin, 1-N-(dimethylamino-carbamoyl)-sisomicin, 1-N-([N-hydroxyethyl-N-methylamino]-carbamoyl)-sisomicin, 1-N-(morpholino-carbamoyl)-sisomicin, 1-N-(hydroxy-carbamoyl)-sisomicin, 1-N-(N-methoxy-carbamoyl)-sisomicin, 1-N-(N-methoxy-N-methyl-carbamoyl)-sisomicin, 1-N-(ethoxy-carbamoyl)-sisomicin, 1-N-(N-ethoxy-N-ethyl-carbamoyl)-sisomicin, 1-N-(propoxy-carbamoyl)-sisomicin, 1-N-(N-ethoxy-N-propyl-carbamoyl)-sisomicin, 1-N-(butoxy-carbamoyl)-sisomicin, 1-N-(tert.-butoxy-carbamoyl)-sisomicin, 1-N-(cyclohexyloxy-carbamoyl)-sisomicin, 1-N-(benzyloxy-carbamoyl)-sisomicin, 1-N-(4-chlorobenzyloxy-carbamoyl)-sisomicin, 1-N-(2,6-dichlorobenzyloxy-carbamoyl)-sisomicin, 1-N-(2-diethylaminoethoxy-carbamoyl)-sisomicin, 1-N-(2-isoxazolinylcarbonyl)-sisomicin, 1-N-(2-tetrahydroisoxazinylcarbonyl)-sisomicin, 1-N-(3-cyanopropyl-carbonyl)-sisomicin, 1-N-(3-chloropropyl-carbamoyl)-sisomicin, 1-N-(cyanomethyl-carbamoyl)-sisomicin, 1-N-(2,2,2-trifluoroethyl-carbamoyl)-sisomicin, 1-N-(N-methyl-N-cyanomethylcarbamoyl)-sisomicin, 1-N-(bis-cyanomethyl-carbamoyl)-sisomicin, 1-N-(aminocarbamoyl)-sisomicin, 1-N-(2,2-di-ethoxyethyl-carbamoyl)-sisomicin, 1-N-(2-hydroxyethoxycarbonylamino-carbamoyl)-sisomicin, 1-N-(D-gluconamido-carbamoyl)-sisomicin, 1-N-(methoxycarbonyl-carbamoyl)-sisomicin, 1-N-(allyloxycarbonyl-carbamoyl)-sisomicin, 1-N-(1-ethoxycarbonylethyl-carbamoyl)-sisomicin, 1-N-(N-methyl-N-morpholinocarbonyl-carbamoyl)-sisomicin, 1-N-(allophanyl)-sisomicin, 1-N-(2-ethoxycarbonylaminoethyl-carbamoyl)-sisomicin, 1-N-(N-methyl-N-aminocarbonylmethyl-carbamoyl)-sisomicin, 1-N-[4-(2-hydroxyethyl)-allophanyl]-sisomicin, 1-N-(2-ureidoethyl-carbamoyl)-sisomicin, 1-N-(2-tetrahydropyranyloxy-carbamoyl)-sisomicin, 1-N-(2,2-dimethyl-1,3-dioxolanyl-5-methyl-carbamoyl)-sisomicin, 1-N-(1,4-dioxaspiro[4,5]decan-2-yl-methyl-carbamoyl)-sisomicin, 1-N-(2-tetrahydrofurylmethyl-carbamoyl)-sisomicin, 1-N-(2,3-dihydroxypropyl-carbamoyl)-sisomicin, 1-N-(2-hydroxyethylcarbamoyl)-sisomicin, 1-N-(2-hydroxy-3-methoxypropyl-carbamoyl)-sisomicin, 1-N-(2-aminoethyl-carbamoyl)-sisomicin, 1-N-(2-morpholinoethyl-carbamoyl)-sisomicin, 1-N-(1-methylpiperidinyl-4-methyl-carbamoyl)-sisomicin, 1-N-[3-(aziridin-1-yl)-propyl-carbamoyl]-sisomicin, 1-N-(4-piperidino-3-hydroxybutyl-carbamoyl)sisomicin, 1-N-[3-bis-(2-hydroxyethyl)-aminopropyl-carbamoyl]-sisomicin, 1-N-[2-(N-2-hydroxyethyl-N-methylamino)-ethyl-carbamoyl]-sisomicin, 1-N-(2-hydroxy-3-diethylaminopropyl-carbamoyl)-sisomicin and 1-N-[3-(4-methyl-1,2,5,6-tetrahydropyridinyl)-propyl-carbamoyl]-sisomicin, Further active compounds according to the invention are the 1-N-aminoalkoxycarbonyl derivatives of sisomicin, examples of which are shown below, that is to say derivatives of sisomicin which carry a group —CO—A on the 1 N atoms, A representing OR. To make reading easier and to give a better summary, only the substituent R is shown:

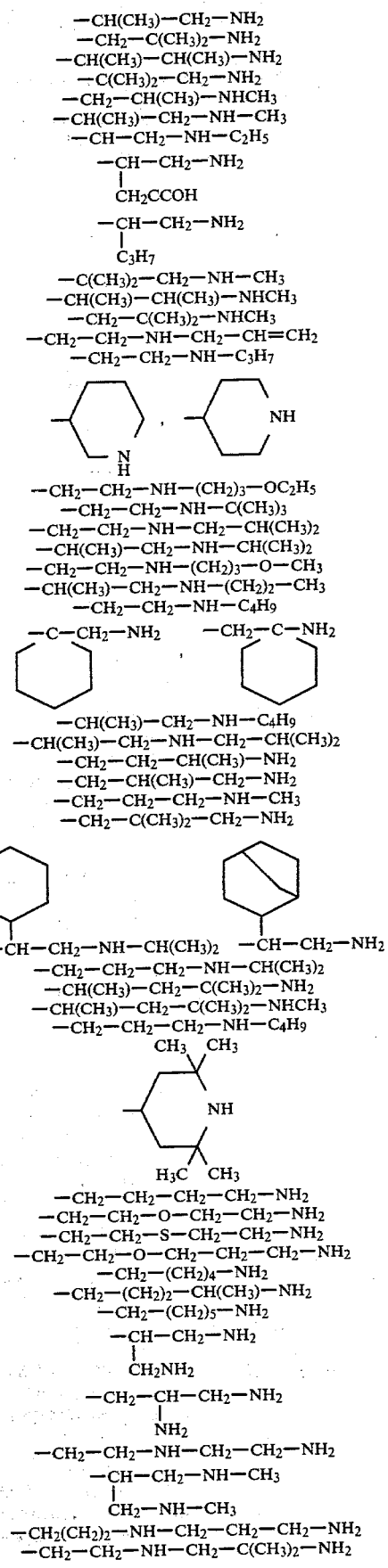

-continued

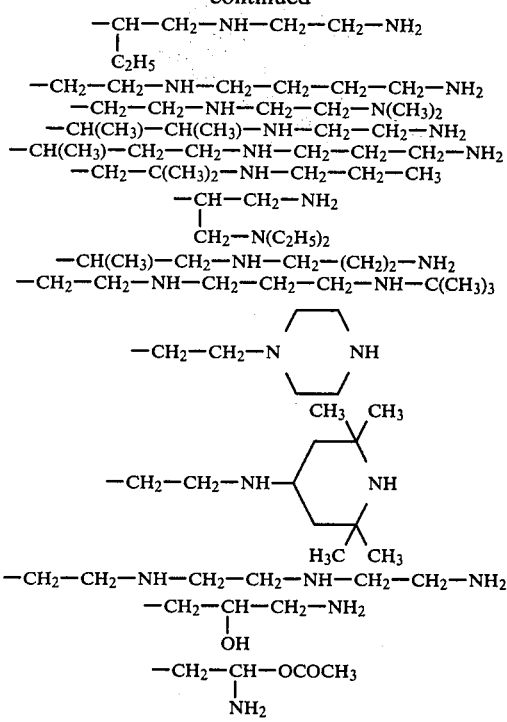

Further antibiotics according to the invention which may be mentioned are: 1-N-hydroxycarbamoyl-gentamicin A, 1-N-hydroxycarbamoyl-gentamicin B, 1-N-hydroxycarbamoyl-gentamicin $B_1$, 1-N-hydroxycarbamoyl-gentamicin $C_1$, 1-N-hydroxycarbamoyl-gentamicin $C_{1a}$, 1-N-hydroxycarbamoyl-gentamicin $C_2$, 1-N-hydroxycarbamoyl-gentamicin $C_{2a}$, 1-N-hydroxycarbamoyl-gentamicin $C_{2b}$, 1-N-hydroxycarbamoyl-gentamicin $X_2$, 1-N-hydroxycarbamoyl-verdamicin, 1-N-hydroxycarbamoyl-tobramicin, 1-N-hydroxycarbamoyl-antibioticium G-418, 1-N-hydroxycarbamoyl-antibioticum 66-40B, 1-N-hydroxycarbamoyl-antibioticum 66-40D, 1-N-hydroxycarbamoyl-antibioticum JI-20A, 1-N-hydroxycarbamoyl-antibioticum JI-20B, 1-N-hydroxycarbamoyl-antibioticum G 52, 1-N-hydroxycarbamoyl-mutamicin 1, 1-N-hydroxycarbamoyl-mutamicin 2, 1-N-hydroxycarbamoyl-mutamicin 4, 1-N-hydroxycarbamoyl-mutamicin 5, 1-N-hydroxycarbamoyl-mutamicin 6, 1-N-(2-amino-ethoxycarbonyl)-gentamicin A, 1-N-(2-amino-ethoxycarbonyl)-gentamicin B, 1-N-(2-amino-ethoxycarbonyl)-gentamicin $B_1$, 1-N-(2-amino-ethoxycarbonyl)-gentamicin $C_1$, 1-N-(2-amino-ethoxycarbonyl)-gentamicin $C_{1a}$, 1-N-(2-amino-ethoxycarbonyl)-gentamicin $C_2$, 1-N-(2-amino-ethoxycarbonyl)-gentamicin $C_{2a}$, 1-N-(2-aminoethoxycarbonyl)-gentamicin $C_{2b}$, 1-N-(2-amino-ethoxycarbonyl)-gentamicin $X_2$, 1-N-(2-amino-ethoxycarbonyl)-verdamicin, 1-N-(2-amino-ethoxycarbonyl)-tobramicin, 1-N-(2-amino-ethoxycarbonyl)-antibioticum G-418, 1-N-(2-amino-ethoxycarbonyl)-antibioticum 66-40B, 1-N-(2-amino-ethoxycarbonyl)-antibioticum 66-40D, 1-N-(2-amino-ethoxycarbonyl)-antibioticum JI-20A, 1-N-(2-amino-ethoxy-carbonyl)-antibioticum JI-20B, 1-N-(2-amino-ethoxycarbonyl)-antibioticum G 52, 1-N-(2-aminoethoxycarbonyl)-mutamicin 1, 1-N-(2-amino-ethoxycarbonyl)-mutamicin 2, 1-N-(2-amino-ethoxycarbonyl)-mutamcin 4, 1-N-(2-amino-ethoxycarbonyl)-mutamicin 5 and 1-N-(2-amino-ethoxycarbonyl)-mutamicin 6.

It has furthermore been found that the 1-N-4,6-di-O-(aminoglycosyl)-1,3-diamino-cyclitol derivatives of the formula I are obtained when a compound of the formula III

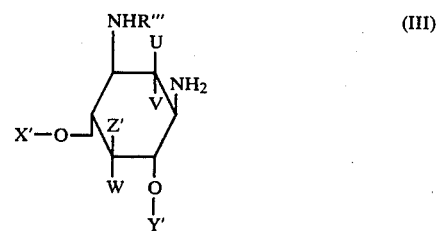

in which

X' denotes a radical of the general formula

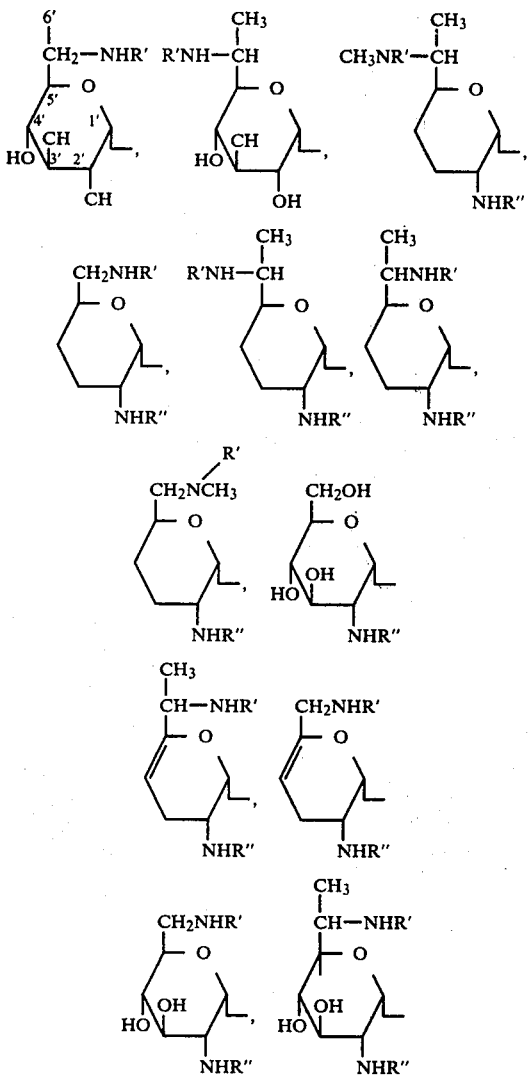

-continued

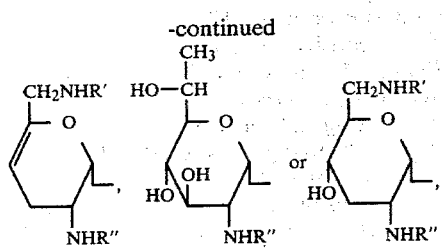

Y' denotes a radical of the general formula

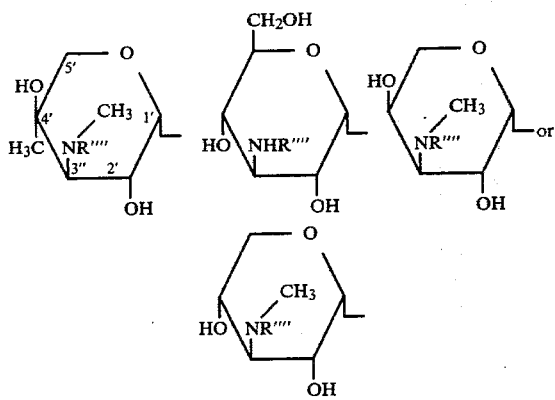

U, V and W independently denote a hydrogen atom or a hydroxyl group and

Z' denotes a hydrogen atom, a hydroxyl group or —NHR$^V$, in which

R', R'', R''', R'''' and R$^V$ independently denote a hydrogen or an amino protective group which can be easily split off under the reaction conditions, or their salts which contain an inorganic or organic acid radical, are reacted in a manner which is in itself known with an acylating agent of the formula IV

 (IV)

in which

A' has the meaning indicated above for A, with the exception that any free amino groups present in A are blocked with the customary amino-protective groups, such as are known, for example, from the literature reference Houben-Weyl, Methoden der Organischen Chemie (Methods of Organic Chemistry), volume XV/1, pages 46–305, Georg Thieme Verlag, Stuttgart, 1974, but preferably with the o-nitrophenyl-sulphenyl protective group, and E denotes a halogen atom, preferably Cl or Br, N$_3$, —O—CO—O—R*, —OR* having the meaning of A' indicated above, phenoxy, 4-nitrophenoxy, 2,4,5-trichlorophenoxy or

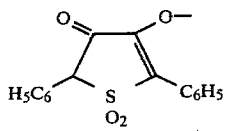

and the mixture is worked up in the customary manner, the protective groups being split off if appropriate, to give compounds of the formula I, or these are converted into their salts, preferably their pharmaceutically usable salts.

Furthermore, compounds of the formula Ia

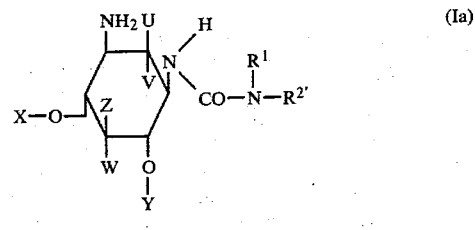 (Ia)

in which

X, Y, U, V, W, Z and R$^1$ have the meaning indicated above and

R$^{2'}$ has the meaning of R$^2$ indicated above, with the exception of alkoxycarbonyl and

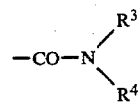

are obtained when a compound of the formula V

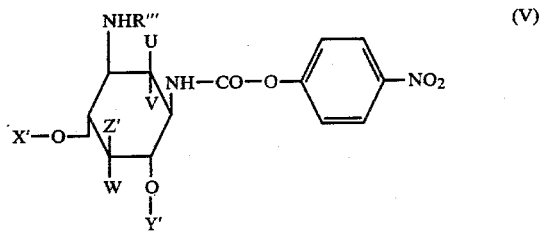 (V)

in which

X', Y', U, V, W and Z' have the meaning indicated above, is reacted with an amine of the formula VI

 (VI)

wherein

R$^1$ and R$^{2'}$ have the meaning indicated above, the protective groups are split off and the 1-N-4,6-di-O-(aminoglycosyl)-1,4-diamino-cyclitol derivatives are optionally converted into their salts, preferably their pharmaceutically usable salts by reaction with suitable acids.

In addition, compounds of the formula Ib

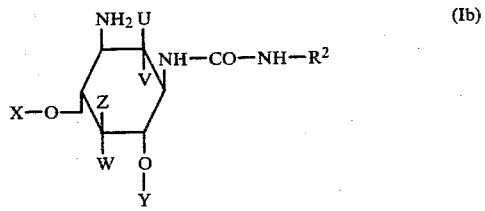 (Ib)

in which

X, Y, U, V, W, Z and R$^2$ have the meaning indicated above, are obtained when compounds of the formula III are reacted with an isocyanate of the formula VII $R^2$—NCO  (VII)

wherein
$R^2$ has the meaning indicated above,
the protective groups are split off and the 1-N-4,6-di-O-(aminoglycosyl)-1,3-diamino-cyclitol derivates are optionally converted into their salts, preferably their pharmaceutically usable salts by reaction with suitable acids.

By protective groups which can be easily split off, there are to be understood those groups which are used for protecting amino groups in peptide syntheses and can be removed again by hydrolysis under mild conditions, hydrogen-olysis under mild conditions or nucleophilic displacement reactions, the 1-N-acyl group introduced being retained and without affecting the 4,6-di-O-(aminoglycosyl)-1,3-diamino-cyclitol skeleton. Several such protective groups are known (Houben-Weyl, Methoden der Organischen Chemie (Methods of Organic Chemistry), volume XV/1, pages 46–305, Georg-Thieme Verlag, Stuttgart 1974).

According to formula III, one of the N atoms or all the N atoms except for 1-N can be blocked; furthermore, it is possible to use the free 4,6-di-O-(aminoglycosyl)-1,3-diamino-cyclitols or their acid addition salts as starting materials.

The following radicals may be mentioned as examples of N-protective groups $R'$, $R''$, $R'''$, $R''''$ and $R^V$: o-nitrophenylsulphenyl, 2,4-dinitrophenylsulphenyl, pentachlorophenylsulphenyl, tritylsulphenyl, carbobenzoxy, phthaloyl, tert.-butoxycarbonyl and trifluoroacetyl.

Surprisingly, the derivatives according to the invention and their pharmaceutically usable salts show a higher action against resistant bacteria strains, coupled with good compatibility, than the compounds known from the state of the art. The substances according to the invention thus represent an enrichment of pharmacy.

If 2',3,3'',6'-tetra-N-(o-nitrophenylsulphenyl)-sisomicin and 4-(2,2-dimethyl-1,3-dioxolan-4-yl-methoxycarbonyloxy)-3-oxo-2,5-diphenyl-2,3-dihydrothiophene 1,1-dioxide are used as starting materials, the course of the reaction can be represented by the equation which follows:

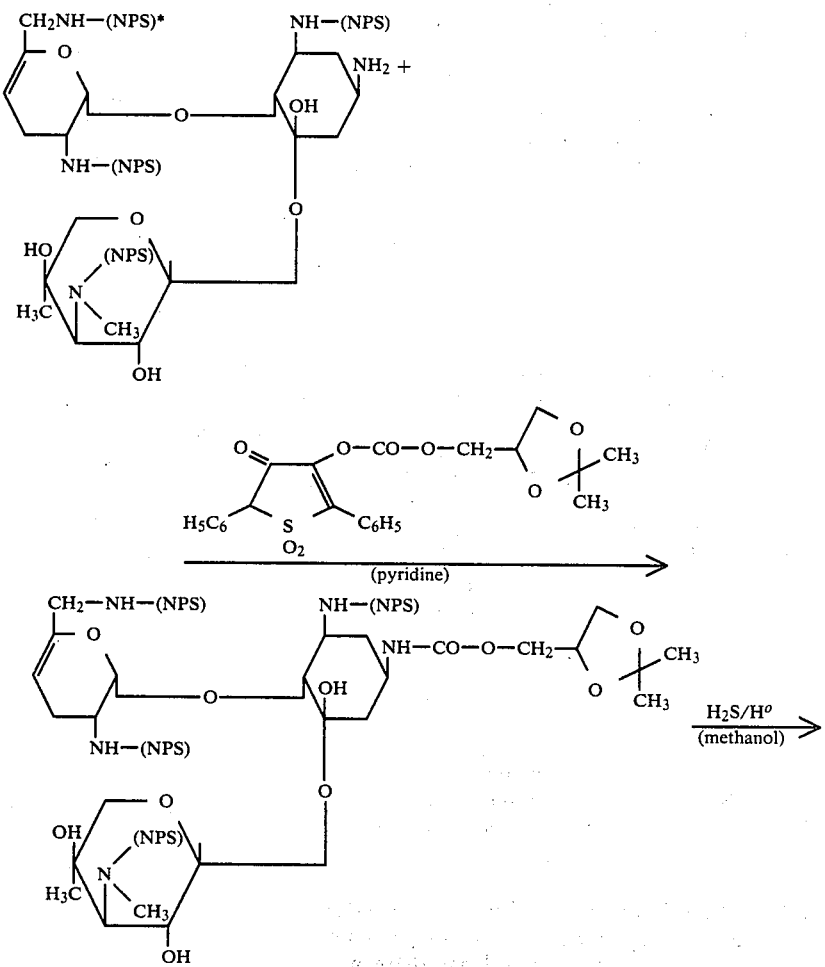

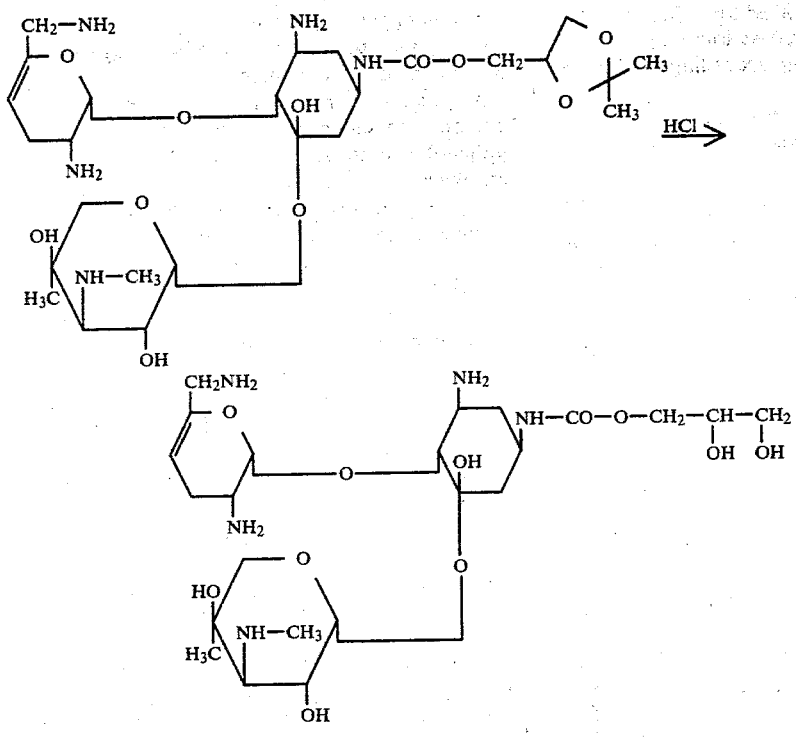

-continued

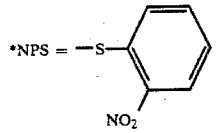

If 2′,3″,6′-tetra-N-(o-nitrophenylsulphenyl)-1-N-(p-nitrophenoxycarbonyl)-sisomicin and hydroxylamine are used as starting materials, the course of the reaction can be represented by the equation which follows:

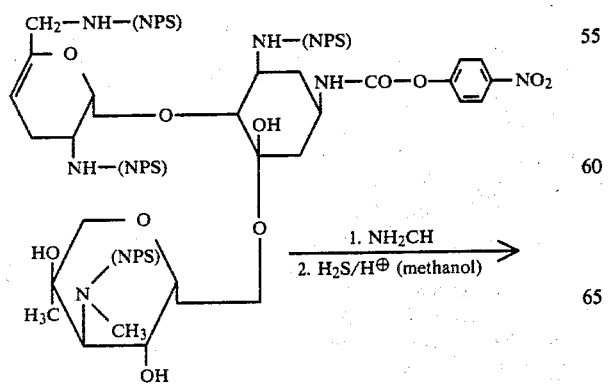

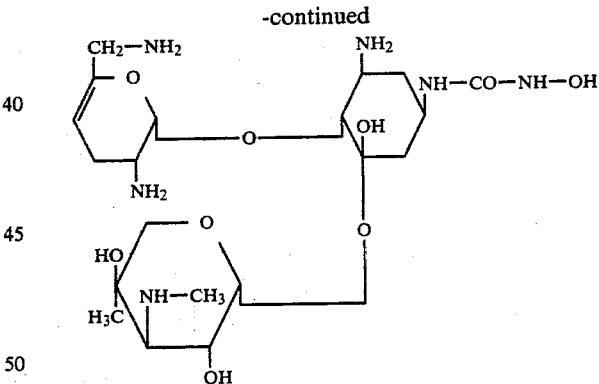

The 4,6-di-O-(aminoglycosyl)-1,3-diamino-cyclitols of the formula VIII

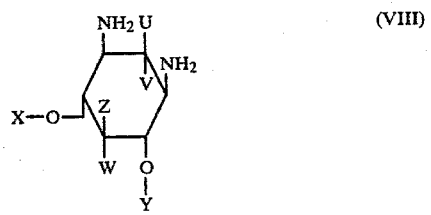

in which
X, Y, U, V, Z and W have the meaning indicated above, used as starting materials for forming the derivatives are known (see, for example, DT-OS (German Published Specification) No. 2,437,160 and DT-OS (German Published Specification) No. 2,552,799) or can be prepared by known processes.

Those N-protected derivatives according to the formulae III and V in which

R', R'', R''', R'''' and $R^V$ represent sulphenyl protective groups of the —SR$^5$ type, wherein R$^5$ denotes phenyl, substituted phenyl or di- or triphenylmethyl, are preferably used in the process for the preparation of the 1-N-4,6-di-O-(aminoglycosyl)-1,3-diamino-cyclitol derivatives according to the invention.

For the preparation of 4,6-di-O-(aminoglycosyl)-1,3-diaminocyclitols protected in this manner, compounds of the formula VIII are reacted, according to a new process (German Patent Application No. P 2,726,197.8-Le A 18 047), with about 3 to 4 equivalents of a compound of the formula IX $$R^5—S—G \qquad (IX)$$

in which

R$^5$ has the meaning indicated above and

G designates halogen or a leaving group which is customary in sulphenylation reactions, in an inert solvent at temperatures between about −30° C. and +50° C. in the presence of a base, and the reaction product is worked up in the customary manner.

Examples which may be mentioned of compounds protected in this manner are: 2',3,3'',6'-tetra-N-(o-nitrophenylsulphenyl)-sisomicin, 2',3,3'',6'-tetra-N-(2,4-dinitrophenylsulphenyl)-sisomicin, 2',3,3'',6'-tetra-N-(pentachlorophenylsulphenyl)-sisomicin, 2',3,3'',6'-tetra-N-(tritylsulphenyl)-sisomicin, 2',3,3'',6'-tetra-N-(butoxycarbonyl)-sisomicin and 2',3,3'',6'-tetra-N-(trifluoroacetyl)-sisomicin.

The starting materials of the formulae IV and VII used as acylating agents are known or can be obtained by processes which are known in principle. Thus, the 4-acyloxy-3-oxo-2,5-diphenyl-2,3-dihydrothiophene 1,1-dioxides used can be obtained, for example, by warming 4,6-diphenylthieno[3,4-d][1,3]dioxol-2-one 5,5-dioxide (compare Angew. Chem. 88, 480 (1976)) with alcohols or amines in inert solvents, such as toluene or acetonitrile.

The (o-nitrophenylsulphenyl-aminoalkyl)-(p-nitrophenyl) carbonates employed are obtained by reacting the (o-nitrophenylsulphenyl)-aminoalcohols with chlorocarbonic acid p-nitrophenyl ester in the presence of an acid-binding agent, such as, for example, triethylamine, in inert diluents, such as methylene chloride or acetonitrile.

Examples of acylating agents which may be mentioned are: chlorocarbonic acid methyl ester, chlorocarbonic acid ethyl ester, chlorocarbonic acid propyl ester, chlorocarbonic acid isopropyl ester, chlorocarbonic acid cyclohexyl ester, chlorocarbonic acid 2,2,2-trichloroethyl ester, chlorocarbonic acid 2-bromoethyl ester, chlorocarbonic acid 4-nitrophenyl ester, tert.-butoxycarbonyl azide, pyrocarbonic acid dimethyl ester, pyrocarbonic acid diethyl ester, pyrocarbonic acid di-tert.-butyl ester, methoxycarbamic acid phenyl ester, N-methoxy-N-methyl-carbamic acid 2,4,5-trichlorophenyl ester, dimethylcarbamic acid chloride, 4-diethylaminocarbonyloxy-3-oxo-2,5-diphenyl-2,3-dihydrothiophene 1,1-dioxide, 4-benzylaminocarbonyloxy-3-oxo-2,5-diphenyl-2,3-dihydrothiophene 1,1-dioxide, methyl isocyanate, ethyl isocyanate, propyl isocyanate, isopropyl isocyanate, butyl isocyanate, isobutyl isocyanate, pentyl isocyanate, hexyl isocyanate, methoxymethyl isocyanate, ethoxymethyl isocyanate, propoxymethyl isocyanate, hexyloxymethyl isocyanate, 2-methoxyethyl isocyanate, 2-chloroethyl isocyanate, cyclohexyl isocyanate, phenyl isocyanate, 4-methoxyphenyl isocyanate, methoxycarbonyl isocyanate, ethoxycarbonyl isocyanate, phenoxycarbonyl isocyanate, isocyanatoacetic acid ethyl ester and 1-β-isocyanato-tetra-O-acetyl-D-glucose.

Examples of new acylating agents which may be mentioned are: 4-methoxycarbonyloxy-3-oxo-2,5-diphenyl-2,3-dihydrothiophene 1,1-dioxide, 4-ethoxycarbonyloxy-3-oxo-2,5-diphenyl-2,3-dihydrothiophene 1,1-dioxide, 4-propoxycarbonyloxy-3-oxo-2,5-diphenyl-2,3-dihydrothiophene 1,1-dioxide, 4-isopropoxycarbonyloxy-3-oxo-2,5-diphenyl-2,3-dihydrothiophene 1,1-dioxide, 4-butoxycarbonyloxy-3-oxo-2,5-diphenyl-2,3-dihydrothiophene 1,1-dioxide, 4-cyclohexyloxycarbonyloxy-3-oxo-2,5-diphenyl-2,3-dihydrothiophene 1,1-dioxide, 4-cyclopropylmethoxycarbonyloxy-3-oxo-2,5-diphenyl-2,3-dihydrothiophene 1,1-dioxide, 4-benzyloxycarbonyloxy-3-oxo-2,5-diphenyl-2,3-dihydrothiophene 1,1-dioxide, 4-allyloxycarbonyloxy-3-oxo-2,5-diphenyl-2,3-dihydrothiophene 1,1-dioxide, 4-propargyloxycarbonyloxy-3-oxo-2,5-diphenyl-2,3-dihydrothiophene 1,1-dioxide, 4-(2-phenoxyethoxycarbonyloxy)-3-oxo-2,5-diphenyl-2,3-dihydrothiophene 1,1-dioxide, 4-(2,2-dimethyl-1,3-dioxolanyl-4-methoxycarbonyloxy)-3oxo-2,5-diphenyl-2,3-dihydrothiophene 1,1-dioxide, 4-(tetrahydrofuryl-2-methoxycarbonyloxy)-3-oxo-2,5-diphenyl-2,3-dihydrothiophene 1,1-dioxide, 4-(tetrahydropyranyl-2-methoxycarbonyloxy)-3-oxo-2,5-diphenyl-2,3-dihydrothiophene 1,1-dioxide, 4-(1,2,5,6-di-O-isopropylidene-α-D-glucofuranosyl-3-carbonyloxy)-3-oxo-2,5-diphenyl-2,3-dihydrothiophene 1,1-dioxide, 4-isobutoxycarbonyloxy-3-oxo-2,5-diphenyl-2,3-dihydrothiophene 1,1-dioxide, 4-tert.-butoxycarbonyloxy-3-oxo-2,5-diphenyl-2,3-dihydrothiophene 1,1-dioxide, 4-sec.-butoxycarbonyloxy-3-oxo-2,5-diphenyl-2,3-dihydrothiophene 1,1-dioxide, 4-(2-chloroethoxycarbonyloxy)-3-oxo-2,5-diphenyl-2,3-dihydrothiophene 1,1-dioxide, 4-(4-chlorobutoxycarbonyloxy)-3-oxo-2,5-diphenyl-2,3-dihydrothiophene 1,1-dioxide, 4-pentyloxycarbonyloxy-3-oxo-2,5-diphenyl-2,3-dihydrothiophene 1,1-dioxide, 4-(3-methylbutoxycarbonyloxy)-3-oxo-2,5-diphenyl-2,3-dihydrothiophene 1,1-dioxide, 4-(2,2-dimethyl-propoxycarbonyloxy)-3-oxo-2,5-diphenyl-2,3-dihydrothiophene 1,1-dioxide, 4-heptyloxycarbonyloxy-3-oxo-2,5-diphenyl-2,3-dihydrothiophene 1,1-dioxide, 4-decyloxycarbonyloxy-3-oxo-2,5-diphenyl-2,3-dihydrothiophene 1,1-dioxide, 4-(2-methoxyethoxycarbonyloxy)-3-oxo-2,5-diphenyl-2-3-dihydrothiophene 1,1-dioxide, 4-(2,3-dimethoxy-propoxycarbonyloxy)-3-oxo-2,5-diphenyl-2,3-dihydrothiophene 1,1-dioxide, 4-(2-hydroxyethoxycarbonyloxy)-3-oxo-2,5-diphenyl-2,3-dihydrothiophene 1,1-dioxide, 4-(2,2-dimethoxy-ethoxycarbonyloxy)-3-oxo-2,5-diphenyl-2,3-dihydrothiophene 1,1-dioxide, 4-(2-dimethylaminoethoxycarbonyloxy)-3-oxo-2,5-diphenyl-2,3-dihydrothiophene 1,1-dioxide and 4-cyclopentyloxycarbonyloxy-3-oxo-2,5-diphenyl-2,3-dihydrothiophene 1,1-dioxide.

New acylating agents of the formula IV in which amino groups present are blocked by the o-nitrophenylsulphenyl (NPS) protective group are listed below. These new compounds correspond to the formula A'—CO—E
wherein
E represents p-nitrophenoxy,
A' can assume, for example the following meaning:
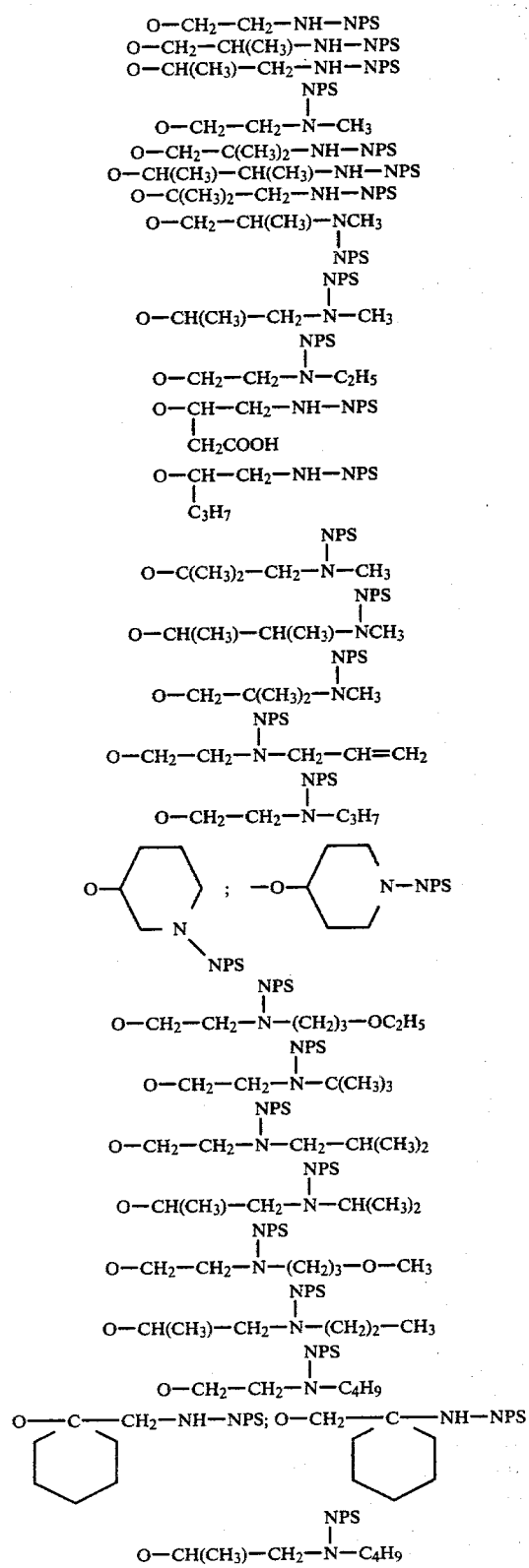
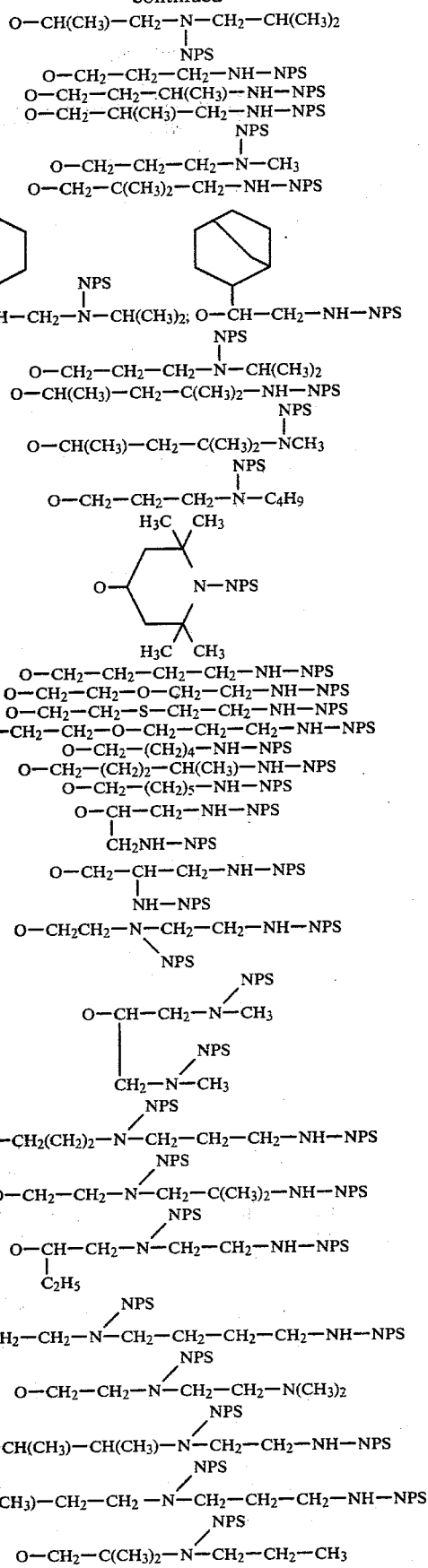

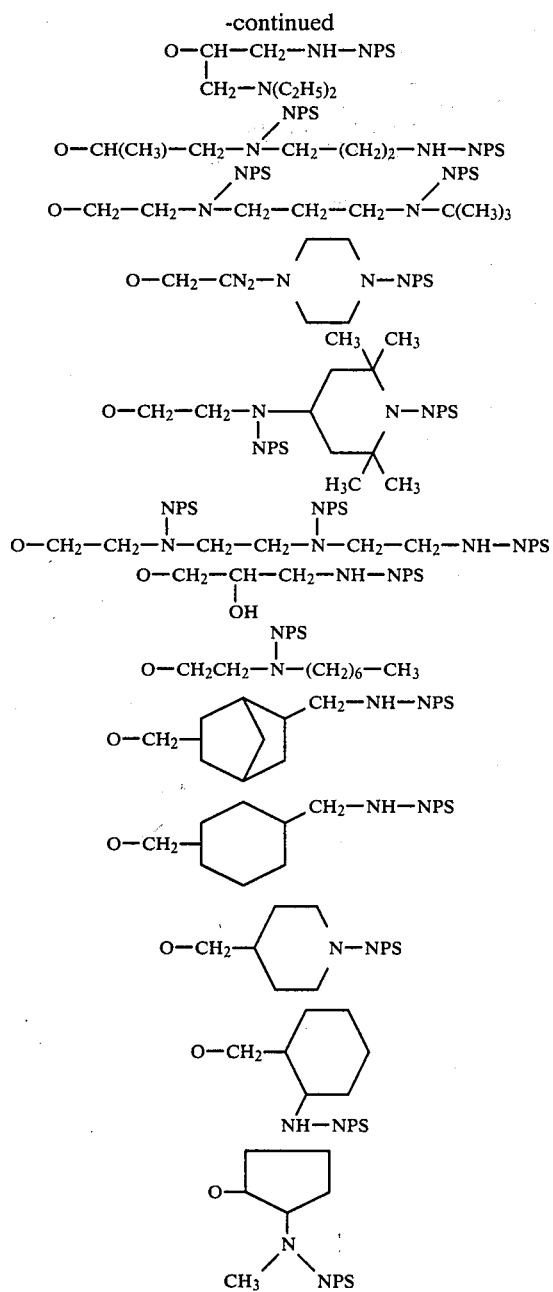

The compounds of the formula V used as intermediate products are also new and are prepared by acylating compounds of the formula III with chloroformic acid p-nitrophenyl ester by the process described in this Application.

The amino compounds of the formula VI are known. Examples which may be mentioned are: ammonia, methylamine, dimethylamine, ethylamine, ethylmethylamine, diethylamine, propylamine, methylpropylamine, dipropylamine, butylamine, isobutylamine, tert.-butylamine, sec.-butylamine, pentylamine, tert.-pentylamine, 2-ethylhexylamine, decylamine, 2-hydroxyethylamine, 2-methylaminoethanol, 1-amino-2-propanol, bis-(2-hydroxypropyl)-amine, 4-amino-2-butanol, 2-amino-2-methyl-propanol, 2-amino-2-methyl-1,3-propanediol, 2-amino-1-hydroxymethyl-1,3-propanediol, 2-methoxyethylamine, 3-chloropropylamine, 3-cyanopropylamine, 3-methylaminopropanenitrile, allylamine, dialylamine, propargylamine, 2,2-dimethoxyethylamine, 2-hydroxy-4-allyloxypropylamine, methylaminoacetamide, 1-amino-2-dimethylaminoethane, 1-amino-2-diethylaminoethane, 1-amino-3-dimethylaminopropane, 1-amino-3-diethylaminopropane, alanine ethyl ester, cyclohexylamine, N-methylcyclohexylamine, N-(2-hydroxyethyl)-cyclohexylamine, 1-(cyclohexylamino)-2-propanol, aminomethylcyclohexane, pyrrolidine, piperidine, morpholine, 1-methylpiperazine, 1-(2-hydroxyethyl)-piperazine, hexamethyleneimine, N,N-dimethylhydrazine, N-hydroxyethyl-N-methyl-hydrazine, 4-aminomorpholine, hydroxylamine, methoxyamine, O,N-dimethylhydroxylamine, ethoxyamine, O,N-diethylhydroxylamine, propoxyamine, O-ethyl-N-propyl-hydroxylamine, butoxyamine, tert.-butoxyamine, cyclohexyloxyamine, benzyloxyamine, 4-chlorobenzyloxyamine, 2,6-dichlorobenzyloxyamine, O-(2-diethylaminoethyl)-hydroxylamine, isoxazolidine and tetrahydroisoxazine.

Possible diluents are all the inert organic solvents. These include, preferably, toluene, chloroform, methylene chloride, dimethylformamide, dimethylacetamide, dimethylsulphoxide, ethers, such as diethyl ether, dioxane and tetrahydrofurane, pyridine, alcohols, such as methanol and ethanol, and mixtures thereof.

If acid-binding agents are required, all the customary organic and inorganic acid-binding agents can be used. These include, preferably, alkali metal hydroxides and alkaline earth metal hydroxides, such as sodium hydroxide, potassium hydroxide or calcium hydroxide, alkali metal carbonates and bicarbonates and alkaline earth metal carbonates and bicarbonates, such as sodium carbonate, potassium carbonate, sodium bicarbonate and calcium carbonate, calcium oxide, tertiary aliphatic and aromatic amines, such as triethylamine and N,N-dimethylaniline, and heterocyclic bases, such as pyridine and quinoline.

The reaction temperatures can be varied within a wide range. In general, the reaction is carried out at temperatures from about $-30°$ C. to $+80°$ C., preferably between $0°$ C. and about $+25°$ C.

The reaction can be carried out under normal pressure, but also under increased pressure. In general, it is carried out under normal pressure.

In carrying out the process according to the invention, 1 mol of the compound of the formula III is reacted with about 1 to 3 mols, preferably with 1.1 to 1.5 mols, of a compound of the formula IV or VII, or 1 mol of the compound of the formula V is reacted with about 1 to 3 mols, preferably 1.1 to 1.5 mols, of the compound of the formula VI. The reaction is preferably carried out in pyridine as the diluent, at room temperature. The protective groups are then split off, the reaction mixture is worked up in the customary manner to give the free 1-N derivative and this is optionally converted into the pharmaceutically usable salts. If, for example, the particularly preferred o-nitrophenylsulphenyl protective groups are used, they are split, under mild conditions, with sulphur-containing, nucleophilic reagents, such as, for example, $H_2S$ or thiophenol.

The compounds according to the invention are antimicrobial agents with a broad spectrum of action and a particular activity against Gram-negative bacteria. These properties make it possible to use them as medicaments, in particular in combating diseases caused by bacteria in warm-blooded animals. They are suitable for the prophylaxis and chemotherapy, in medicine, of local and systemic infections, in particular infections of the urogenital system, which are caused by Gram-negative bacteria, for example E. coli, Proteus, Klebsiella and Pseudomonas. In the agar hole test, inhibition areolas were found, for example, against the following strains of bacteria, using a concentration of 100 micrograms/1 ml: *Pseudomonas aerug.* 5737, *Pseudomonas aerug.* F 41, *Klebsiella pneum.* 2 Munich, *Klebsiella pneum.* 1 Düsseldorf, *E. coli* Münster and *E. coli* Neumann.

The process for the treatment of diseases caused by bacteria is characterised in that the new 1-N derivatives are administered to warm-blooded animals suffering from these diseases.

As stated above, the invention also relates to the use in medicine of the compounds of the invention.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, bloodiostonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The product of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above-mentioned diseases in human and non-human animals, which comprises administering to the animals a compound of the invention alone or in admixture with a diluent or in the form of a medicament according to the invention.

It is envisaged that these active compounds will be administered parenterally (for example intramuscularly, intraperitoneally, subcutaneously intravenously), rectally or locally, preferably parenterally or topically. Preferred pharmaceutical compositions and medicaments are therefore those adapted for administration such as parenteral or topical administration. Administration in the method of the invention is preferably parenteral or topical.

In general, the dose to be administered of the compounds of the invention depends on the age and weight of the organism, on the nature of the administration and on the type and severity of the bacterial infection. The dosage of the compounds according to the invention is usually similar to the dosage of the 1-N-unsubstituted compounds. The dosage range is from 20 mg/day to 2,000 mg/day/warmblooded animal, preferably 100 mg-500 mg/day.

The compounds of the invention can be administered orally. They can be administered in single administrations, or the administration can be divided into several administrations. They can also be applied topically in the form of ointments, creams or lotions. Pharmaceutical excipients for these formulations include water, oils, fats, polyesters and polyols.

As will be shown below, the process for the preparation of medicaments which contain the new 1-N-sisomicin derivatives is characterised in that the new compounds are mixed with pharmaceutically suitable excipients and/or additives.

Tablets, capsules or elixirs can be used for oral administration of the compounds of this invention, but the compounds can also be admixed to the animal feed.

In general, topical formulations contain about 0.1 to about 3.0 g of the compounds of the invention per 100 g of ointment, cream or lotion. Topical application is effected about 2 to 5 times daily.

The antibacterial agents of the invention can be in the liquid form, as solutions or suspensions, for use on the ears and eyes or for parenteral administration in the form of intramuscular injections. Injections solutions or suspensions are usually administered in a manner such that about 1 to 15 mg of active compound per kilogram of body weight enter the infected organism in 2 to 4 doses daily. The precise dose depends on the nature of the infections, on the sensitivity of the infecting germ and on the individual characteristics of the subject to be treated.

| Formulation 1 Tablet | 10 mg tablet | 25 mg tablet | 100 mg tablet |
|---|---|---|---|
| (a) 1-N-(2,3-Dihydroxypropoxycarbonyl)-sisomicin | 10.50+ mg | 26.25+ mg | 105.00+ mg |
| Lactose | 197.50 mg | 171.25 mg | 126.00 mg |
| Maize starch | 25.00 mg | 25.00 mg | 35.00 mg |
| Polyvinylpyrrolidone | 7.50 mg | 7.50 mg | 7.50 mg |
| Magnesium stearate +5% excess | 2.50 mg | 2.50 mg | 3.50 mg |
| (b) 1-N-(Hydroxycarbamoyl)-sisomicin | 10.50+ mg | 26.25+ mg | 105.00+ mg |
| Lactose | 197.50 mg | 171.25 mg | 126.00 mg |
| Maize starch | 25.00 mg | 25.00 mg | 35.00 mg |
| Polyvinylpyrrolidone | 7.50 mg | 7.50 mg | 7.50 mg |
| Magnesium stearate +5% excess | 2.50 mg | 2.50 mg | 3.50 mg |

To product the tablets, a slurry of 1-N-(2,3-dihydroxypropoxycarbonyl)-sisomicin or 1-N-(hydroxycarbamoyl)-sisomicin, lactose and polyvinylpyrrolidone is prepared and this is spray-dried. The maize starch and magnesium stearate are added and the mixture is pressed to tablets.

| Formulation 2 | |
|---|---|
| Ointment | |
| 1-N-(2,3-Dihydroxypropoxycarbonyl)-sisomicin | 1.0 g |
| Methylparaben U.S.P. | 0.5 g |
| Le A 18 364 | |
| Propylparaben U.S.P. | 0.1 g |
| Petrolatum | to 1000 g |

Preparation
(1) The petrolatum is melted;
(2) The 1-N-(2,3-dihydroxypropoxycarbonyl)-sisomicin, methylparaben and propylparaben are mixed with about 10% of the molten petrolatum;
(3) The mixture is introduced into a colloid mill; and
(4) The rest of the petrolatum is added, whilst stirring, and the mixture is cooled until it becomes semi-solid. The product is filled into suitable containers.

| Formulation 3 Injection solution | Per 2.0 ml phial | Per 50 liters |
|---|---|---|
| 1-N-(2,3-Dihydroxypropoxycarbonyl)-sisomicin | 84.0 mg+ | 2100.0 gm |
| Methylparaben, U.S.P. | 3.6 mg | 90.0 gm |
| Propylparaben, U.S.P. | 0.4 mg | 10.0 gm |
| Sodium bisulphite, U.S.P. | 6.4 mg | 160.0 gm |
| Disodium ethylenediaminetetraacetate dihydrate | 0.2 mg | 5.0 gm |
| Water, U.S.P. q.s. | 2.0 mg | 50.0 liters |
| +5% excess | | |

The present invention will now be further illustrated by reference to the Examples in which the examples designated "a" relate to the preparation of starting compounds and the remaining Examples relate to the production of compounds of the invention.

EXAMPLE 1a

4-Ethoxycarbonyloxy-3-oxo-2,5-diphenyl-2,3-dihydro-thiophene 1,1-dioxide

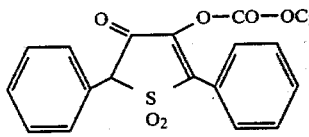

2 g of 4,6-diphenyl-thieno[3,4-d][1,3]dioxol-2-one 5,5-dioxide (Angew. Chem. 88, 480 (1976)) are heated in 40 ml of ethanol until the yellow colour disappears. After cooling, 1.2 g of 4-ethoxycarbonyloxy-3-oxo-2,5-diphenyl-2,3-dihydrothiophene 1,1-dioxide, which contains a trace of 4-hydroxy-3-oxo-2,5-diphenyl-2,3-dihydrothiophene 1,1-dioxide as an impurity, are obtained; melting point 132°–133° C. (decomposition).

$C_{19}H_{16}O_6S$ (372.4): Calculated: C 61.28; H 4.33. Found: 61.4; 4.6.

IR (KBr): 1723 and 1772 cm$^{-1}$;

NMR (CDCl$_3$): δ1.34 t (CH$_3$), 4.3 q (O—CH$_2$), 5.17 s (CH), 7.1–7.65 m (8 aromatic protons) and 7.7–8.15 m (2 aromatic protons) [ppm];

Mass spectrum (70 eV): m/e 328 (372-CO$_2$), 300 (372-CO$_2$C$_2$H$_4$) and 264.

The corresponding intermediate products of Table I are prepared analogously to Example 1a. In these preparations, in the case of alcohols with a boiling point >100° C., the reaction should appropriately be carried out using equivalent amounts of an inert solvent, such as toluene or acetonitrile. The reaction products frequently contain a proportion of 4-hydroxy-3-oxo-2,5-diphenyl-2,3-dihydrothiophene 1,1-dioxide to a greater or lesser extent, which does not interfere in the subsequent reaction and therefore does not need to be removed.

TABLE 1

Intermediate products of the formula

| Example No. | R | IR (KBr) (cm$^{-1}$) |
|---|---|---|
| 2a | CH$_3$ | 1730, 1780 |
| 3a | C$_3$H$_7$ | 1730, 1775 |
| 4a | C$_4$H$_2$ | 1730, 1775 |
| 5a | CH(CH$_3$)$_2$ | 1725, 1770, 1785 |
| 6a | CH$_2$—CH(CH$_3$)$_2$ | 1728, 1780 |
| 7a | C(CH$_3$)$_3$ | |
| 8a | CH(CH$_3$)(C$_2$H$_5$) | 1729, 1778 |
| 9a | C$_5$H$_{11}$ | 1728, 1775 |
| 10a | CH$_2$—CH$_2$—CH(CH$_3$)$_2$ | 1725, 1777 |
| 11a | CH$_2$—C(CH$_3$)$_3$ | 1729, 1780 |
| 12a | (CH$_2$)$_7$—CH$_3$ | 1728, 1780 |
| 13a | CH$_2$CH$_2$Cl | 1729, 1780 |
| 14a | (CH$_2$)$_4$Cl | 1720, 1777 |
| 15a | CH$_2$CH$_2$OCH$_3$ | 1730, 1782 |
| 16a | CH$_2$CH$_2$CN | 1725, 1780, 2260 |
| 17a | CH$_2$—cyclopropyl | 1728, 1778 |
| 18a | CH$_2$—cyclohexyl | 1730, 1778 |
| 19a | cyclohexyl (methyl-substituted) | 1730, 1770 |
| 20a | bornyl group | 1725, 1770, 1730, 1775 |
| 21a | CH$_2$—CH=CH$_2$ | 1728, 1778 |
| 22a | CH$_2$—C≡CH | 1731, 1787 |
| 23a | CH$_2$—CH$_2$—O—C$_8$H$_3$ | 1730, 1775 |
| 24a | CH$_2$—C$_8$H$_3$ | |
| 25a | CH$_2$—(2,2-dimethyl-1,3-dioxolan-4-yl) | 1725, 1778 |
| 26a | CH$_2$—(2,2-divinyl-1,3-dioxolan-4-yl) | 1729, 1780 |
| 27a | CH$_3$—CH—(1,4-dioxaspiro[4.5]decyl) | 1730, 1780 |
| 28a | CH$_2$—tetrahydrofuran-2-yl | 1728, 1778 |
| 29a | CH$_2$—tetrahydropyran-2-yl | 1730, 1782 |
| 30a | diacetone-galactose derivative | 1725, 1780 |
| 31a | 2-methoxy-tetrahydropyranyl | 1730, 1780 |

TABLE 1-continued

Intermediate products of the formula

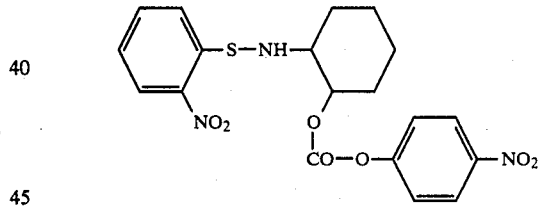

| Example No. | R | IR (KBr) (cm$^{-1}$) |
|---|---|---|
| 32a | CH$_2$—[cyclobutane with O], C$_2$H$_5$ | 1730, 1782 |
| 33a | —CH(CH$_2$—OCH$_3$)$_2$ | 1730, 1783 |
| 34a | —CH(CH$_2$—OC$_2$H$_5$)$_2$ | 1730, 1789 |
| 35a | CH$_2$—CO$_2$—C$_4$H$_9$ | 1729, 1753, 1790 |
| 36a | —CH(CH$_3$)(CO$_2$—C$_2$H$_5$) | 1729, 1733, 1786 |
| 37a | CH$_2$—[dioxolane with phenyl], C$_2$H$_5$ | 1730, 1781 |
| 38a | CH$_2$CH$_2$—S—CH$_3$ | 1730, 1782 |
| 39a | [dioxolane with phenyl] | 1732, 1780 |
| 40a | [tetrahydrofuran] | 1728, 1778 |

EXAMPLE 41a (4-Nitrophenyl)-[2-(-nitrophenylsulphenyl-methyl-amino)-ethyl]-carbonate

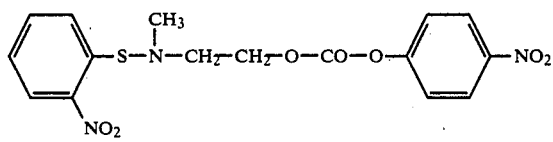

A solution of 1.4 g of 2-methylamino-ethanol in 30 ml of dioxane is initially introduced and a solution of 3.8 g of o-nitrophenylsulphenic acid chloride in 10 ml of dioxane and 8.5 ml of 2 N sodium hydroxide solution are simultaneously added dropwise whilst maintaining the pH at 8. After stirring the mixture at room temperature for several hours, it is concentrated in vacuo, the residue is taken up in ethyl acetate and the ethyl acetate mixture is washed twice with water, dried with Na$_2$SO$_4$ and concentrated in vacuo. The oil which remains is chromatographed on 100 g of silica gel with toluene/ethyl acetate (2:1) and the main component (R$_f$: 0.29) is separated off. Yield: 2.9 g of N-(2-hydroxyethyl)-N-methyl-o-nitrosulphenic acid amide; melting point: 53°–56° C.

456 mg of this compound and 600 mg of chloroformic acid p-nitrophenyl ester are dissolved in 5 ml of acetonitrile, and 300 mg of triethylamine in 5 ml of acetonitrile are added, whilst cooling with ice. After 1 hour at room temperature, the mixture is concentrated in vacuo, the residue is taken up in 30 ml of methylene chloride, the methylene chloride mixture is washed twice with water, dried with Na$_2$SO$_4$ and concentrated in vacuo, the resulting orange oil is chromatographed on 100 g of silica gel with toluene/ethyl acetate (2:1) and the main fraction is separated off. Yield: 250 mg of an orange oil which slowly crystallises completely.

IR (KBr): 1770 cm$^{-1}$. R$_f$ value (toluene/ethyl acetate, 2:1): 0.84.

EXAMPLE 42a

4-Nitrophenyl 2-(2-nitrophenylsulphenylamino)-ethyl carbonate

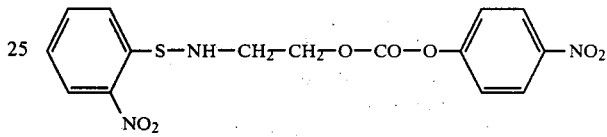

The procedure is analogous to Example 41a; IR: 1770 cm$^{-1}$; R$_f$ value (toluene/ethyl acetate, 2:1): 0.77.

EXAMPLE 43a

4-Nitrophenyl 2-(2-nitrophenylsulphenylamino)-cyclohexyl carbonate

The procedure is analogous to Example 41a; IR: 1770 cm$^{-1}$, R$_f$ value (toluene/ethyl acetate, 2:1): 0.92 (cis-/trans mixture according to NMR).

The examples listed in Table 1A which follows are obtained in a manner corresponding to Example 41a:

TABLE Ia

Intermediate products of the formula

A'—CO—O—[phenyl]—NO$_2$

| Example No. | A' | IR (cm$^{-1}$) |
|---|---|---|
| 44a | O—CH(cyclohexyl)—CH$_2$—N(NPS)—CH(CH$_3$)$_2$ | 1772 |
| 45a | O—CH$_2$CH$_2$—N(NPS)—C$_3$H$_7$ | 1768 |

TABLE Ia-continued

Intermediate products of the formula

A'—CO—O—⟨C6H4⟩—NO2

| Example No. | A' | IR (cm$^{-1}$) |
|---|---|---|
| 46a | O—CH2CH2—N(NPS)—C4H9 | 1770 |
| 47a | O—CH2CH2—N(NPS)—CH2CH(CH3)2 | 1769 |
| 48a | O—CH(CH3)—CH2—N(NPS)—CH3 | 1766 |
| 49a | O—CH2CH2—CH(CH3)—NH—NPS | 1766 |
| 50a | O—CH(CH3)—CH2—C(CH3)2—NH—NPS | 1763 |
| 51a | O—CH(CH3)—CH2—N(NPS)—CH(CH3)2 | 1763 |
| 52a | O—CH2CH2—N(NPS)—(CH2)5—CH3 | 1767 |
| 53a | O—CH2CH2—N(NPS)—C(CH3)3 | 1762 |
| 54a | O—(CH2)3—NH—NPS | 1763 |
| 55a | O—(CH2)4—NH—NPS | 1769 |
| 56a | O—(CH2)5—NH—NPS | 1768 |
| 57a | O—(CH2)6—NH—NPS | 1770 |
| 58a | O—CH(CH3)—CH2—NH—NPS | 1770 |
| 59a | O—CH2CH2OCH2CH2—NH—NPS | 1768 |
| 60a | O—CH2CH2O(CH2)3—NH—NPS | 1770 |
| 61a | O—CH2CH2SCH2CH2—NH—NPS | 1768 |
| 62a | O—CH2—CH2—N(NPS)—(CH2)3—OCH3 | 1770 |
| 63a | O—CH(C2H5)CH2—N(NPS)—CH2CH2—NH—NPS | 1765 |
| 64a | O—CH(CH2—N(CH3)(NPS))(CH2—N(CH3)(NPS)) | 1760 |
| 65a | O—CH2—(cyclohexyl)—NH—NPS | 1780 |
| 66a | O—CH2—(cyclohexyl)—NH—NPS | 1770 |
| 67a | (cyclopentyl with O and N(CH3)(NPS)) | 1767 |
| 68a | (piperidine with O and N—NPS) | 1765 |
| 69a | O—CH2—(piperidine)—N—NPS | 1760 |
| 70a | O—CH2—(norbornyl)—CH2—NH—NPS | 1768 |
| 71a | O—CH2—(cyclohexyl)—CH2—NH—NPS | 1765 |
| 72a | (2,2,6,6-tetramethylpiperidine with O and N) | 1765 |
| 73a | O(CH2)2—N(NPS)—CH—CH=CH2 | 1763 |
| 74a | O(CH2)3—N(NPS)—CH(CH3)2 | 1763 |
| 75a | O(CH2)2—N(NPS)—C2H5 | 1761 |
| 76a | OCH2—CH(NH—NPS)—CH3 | 1762 |
| 77a | O—CH2—C(CH3)2—CH2—NH—NPS | 1762 |
| 78a | O—CH2—CH(CH3)—CH2—NH—NPS | 1770 |
| 79a | O—CH(CH3)—CH2—N(NPS)—CH2—CH(CH3)2 | 1761 |
| 80a | O—(CH2)3—N(NPS)—C4H9(n) | 1763 |
| 81a | O—(CH2)3—CH(NHNPS)—CH3 | 1768 |
| 82a | O—(CH2)2—N(NPS)—(CH2)3—O—C2H5 | 1769 |

TABLE Ia-continued

Intermediate products of the formula

A'—CO—O—⟨C6H4⟩—NO2

| Example No. | A' | IR (cm$^{-1}$) |
|---|---|---|
| 83a | O—CH(CH3)—CH2—N(NPS)—C(CH3)3 | 1762 |
| 84a | O—CH(CH3)—CH2—C(CH3)(CH3)—N(NPS)—CH3 | 1764 |
| 85a | O—CH(CH3)—CH2—N(NPS)—(CH2)4—NH—NPS | 1761 |
| 86a | O—CH2—CH(NHNPS)—COOC2H5 | 1762 |
| 87a | O—CH2-pyrrolidinyl-NPS | 1763 |

EXAMPLE 88a

4-Nitrophenyl 2-triphenylmethoxyethyl carbonate

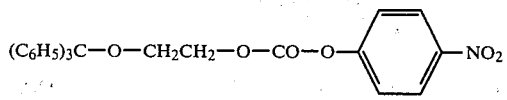

630 mg of chloroformic acid p-nitrophenyl ester are added to 921 mg of O-monotriphenylmethylglycol (J. Chem. Soc. 1960, 2587) in 5 ml of pyridine and the reaction mixture is stirred at room temperature for 30 minutes and concentrated. After chromatography on 50 g of silica gel with toluene as the running agent, 600 mg of 4-nitrophenyl 2-triphenylmethoxyethyl carbonate of melting point 136°–141° C. are obtained; IR: 1775 cm$^{-1}$.

EXAMPLE 89a

4-Nitrophenyl 2-triphenylmethoxyethoxyethyl carbonate

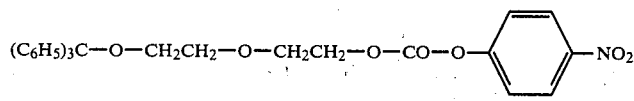

The procedure is analogous to Example 88a; yield: 0.9 g of an oil, IR: 1770 cm$^{-1}$.

EXAMPLE 90a

4-Nitrophenyl 2-dimethylaminoethyl carbonate hydrochloride

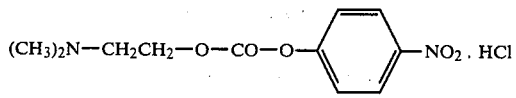

270 mg of 2-dimethylaminoethanol in 5 ml of acetonitrile are stirred with 630 mg of chloroformic acid p-nitrophenyl ester at room temperature for 30 minutes, the mixture is concentrated in vacuo and the residue is stirred with 2 ml of ethyl acetate; yield: 0.4 g; IR: 1770 cm$^{-1}$.

EXAMPLE 91a

4-Nitrophenyl 3-dimethylaminopropyl carbonate hydrochloride

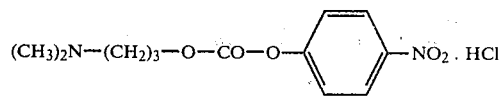

The procedure is analogous to Example 90a; IR: 1768 cm$^{-1}$.

EXAMPLE 92a

4-Nitrophenyl 2-diethylaminoethyl carbonate hydrochloride

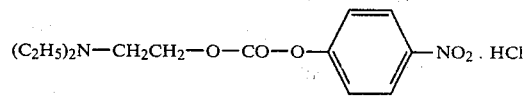

The procedure is analogous to Example 90a; IR: 1760 cm$^{-1}$.

EXAMPLE 1

1-N-Isopropoxycarbonyl-sisomicin 50 mg ($1.3 \times 10^{-4}$ mol) of 4-isopropoxycarbonyloxy-3-oxo-2,5-diphenyl-2,3-dihydrothiophene 1,1-dioxide are added to 110 mg ($10^{-4}$ mol) of 2', 3,3'',6'-tetra-N-(o-nitrophenylsulphenyl)-sisomicin in 0.5 ml of pyridine and the mixture is left to stand at room temperature for one day. Thereafter, it is concentrated in vacuo, the residue is dissolved in 0.3 ml of methylene chloride/methanol (95:5) and the solution is filtered over a silica gel column with methylene chloride/methanol (95:5). The acylation product is thereby separated off from from a by-product, which remains at the start. The eluate is evaporated in vacuo, the residue is taken up in 3 ml of methylene chloride, 0.5 ml of a 4% strength solution of hydrogen sulphide in methanol is added and the mixture is acidified with a few drops of a methanolic hydrogen chloride solution. After 5 minutes, the mixture is extracted twice with 2 ml of water each time, the extracts are extracted by shaking with methylene chloride, the product phase is treated with active charcoal and the almost colourless solution is shaken for a short time with about 1 ml of a basic ion exchanger (Lewatit MP 500). The mixture is evaporated under a high vacuum, the residue is taken up in a little methanol and the methanol mixture is again treated with active charcoal for a short time. After concentrating the solution, 19 mg of 1-N-isopropoxycarbonyl-sisomicin are obtained; R$_f$ value+): 0.61.

+)Unless otherwise indicated, all the $R_f$ values given in the examples were measured on 20×20 thin layer chromatography pre-coated plates silica gel 60 F-254 (MERCK, Darmstadt) in the running agent system methylene chloride/methanol/20% strength ammonia (2:4:1) at room temperature, against sisomicin as a comparison substance ($R_f$=0.24).

The compounds listed in Table II are obtained analogously to Example 1.

TABLE II
Compounds of the formula

| Example No. | R | $R_f$ value(+) |
|---|---|---|
| 2 | $CH_3$ | 0,54 |
| 3 | $C_2H_5$ | 0,65 |
| 4 | $C_3H_7$ | 0,63 |
| 5 | $C_4H_2$ | 0,71 |
| 6 | $CH_2CH(CH_3)_2$ | 0,65 |
| 7 | $C(CH_3)_3$ | 0,79 |
| 8 |  | 0,70 |
| 9 | $C_5H_{11}$ | 0,67 |
| 10 | $CH_2CH_2CH(CH_3)_2$ | 0,69 |
| 11 | $CH_2C(CH_3)_3$ | 0,74 |
| 12 | $(CH_2)_7CH_3$ | 0,72 |
| 13 | $CH_2CH_2Cl$ | 0,57 |
| 14 | $(CH_2)_4Cl$ | 0,63 |
| 15 | $CH_2CH_2-OCH_3$ | 0,65 |
| 16 | 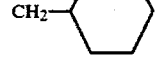 | 0,62 |
| 17 |  | 0,67 |
| 18 | 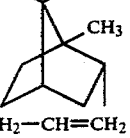 | 0,75 |
| 19 | 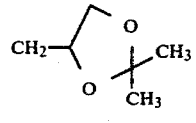 | 0,75 |
| 20 | $CH_2-CH=CH_2$ | 0,72 |
| 21 | $CH_2-C\equiv CH$ | 0,55 |
| 22 | $CH_2CH_2-O-C_8H_8$ | 0,67 |
| 23 | $CH_2-C_8H_5$ | 0,65 |
| 24 |  | 0,55 |

TABLE II-continued
Compounds of the formula

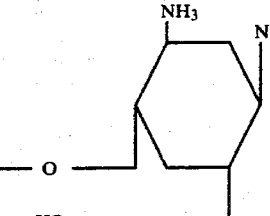

| Example No. | R | $R_f$ value(+) |
|---|---|---|
| 25 | 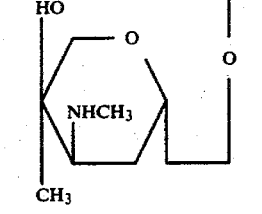 | 0,74 |
| 26 | 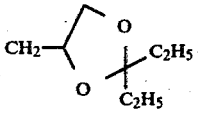 | 0,71 |
| 27 | 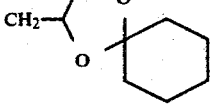 | 0,60 |
| 28 | 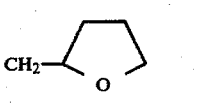 | 0,60 |
| 29 | 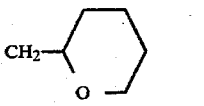 | 0,56 |
| 30 | 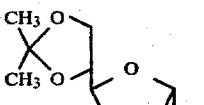 | 0,68 |
| 31 | 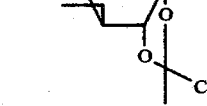 | 0,67 |
| 32 | 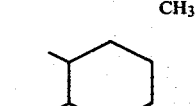 | 0,66 |
| 33 | 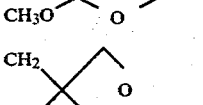 | 0,75 |
| 34 | $CH_2-CO_2-C_4H_9$ | |

TABLE II-continued

Compounds of the formula

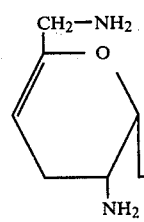

| Example No. | R | $R_f$ value(+) |
|---|---|---|
| 35 | CH(CH₃)CO₂C₂H₅ | 0,50 |
| 36 | CH₂CH₂—NH₂ | 0,28 |
| 37 | CH₂CH₂—NH—CH₃ | 0,30 |
| 38 | 2-aminocyclohexyl | 0,28 |
| 39 | CH(C₆H₁₁)CH₂—NH—CH(CH₃)₂ | 0,62 |
| 40 | CH₂CH₂—NH—C₃H₇-n | 0,46 |
| 41 | CH₂CH₂—NH—C₄H₉-n | 0,50 |
| 42 | CH₂CH₂—NH—CH₂CH(CH₃)₂ | 0,54 |
| 43 | CH(CH₃)CH₂—NH—CH₃ | 0,28 |
| 44 | CH₂CH₂CH(CH₃)—NH₂ | 0,27 |
| 45 | CH(CH₃)CH₂—C(CH₃)₂—NH₂ | 0,36 |
| 46 | CH(CH₃)CH₂—NH—CH(CH₃)₂ | 0,52 |
| 47 | CH₂CH₂—NH—(CH₂)₅CH₃ | 0,56 |
| 48 | CH₂CH₂—NH—C(CH₃)₃ | 0,56 |
| 49 | (CH₂)₃—NH₂ | 0,20 |
| 50 | (CH₂)₄—NH₂ | 0,18 |
| 51 | (CH₂)₅—NH₂ | 0,25 |
| 52 | (CH₂)₆—NH₂ | 0,23 |
| 53 | CH(CH₃)CH₂—NH₂ | 0,49 |
| 54 | CH₂CH₂OCH₂CH₂—NH₂ | 0,30 |
| 55 | CH₂CH₂O(CH₂)₃—NH₂ | 0,15 |
| 56 | CH₂CH₂SCH₂CH₂—NH₂ | 0,38 |
| 57 | CH₂CH₂—NH—(CH₂)₃—OCH₃ | 0,47 |
| 58 | CH(C₂H₅)CH₂—NH—CH₂CH₂—NH₂ | 0,35 |
| 59 | —CH(CH₂NH—CH₃)₂ | 0,16 |
| 60 | 1-aminocyclohexylmethyl | 0,49 |
| 61 | (2-aminocyclohexyl)methyl | 0,43 |
| 62 | 3-(methylamino)cyclopentyl | 0,43 |
| 63 | piperidin-4-yl | 0,28 |
| 64 | (piperidin-4-yl)methyl | 0,16 |
| 65 | norbornyl-CH₂-NH₂ methyl | 0,49 |
| 66 | (aminomethyl)cyclohexylmethyl | 0,35 |
| 67 | 2,2,6,6-tetramethylpiperidin-4-yl | 0,57 |
| 68 | (CH₂)₂—NH—CH₂—CH═CH₂ | 0,56 |
| 69 | (CH₂)₃—NH—CH(CH₃)₂ | 0,51 |
| 70 | (CH₂)₂NH—C₂H₅ | 0,43 |
| 71 | —CH₂—CH(NH₂)—CH₃ | 0,48 |
| 72 | —CH₂—C(CH₃)₂—CH₂—NH₂ | 0,50 |
| 73 | —CH₂—CH(CH₃)—CH₂—NH₂ | 0,29 |
| 74 | —CH(CH₃)—CH₂—NH—CH₂—CH(CH₃)₂ | 0,61 |

TABLE II-continued
Compounds of the formula

| Example No. | R | $R_f$ value[+] |
|---|---|---|
| 75 | —(CH$_2$)$_3$—NH—C$_4$H$_9$(n) | 0,54 |
| 76 | —(CH$_2$)$_3$—CH—CH$_3$<br>　　　　　　　\|<br>　　　　　　　NH$_2$ | 0,32 |
| 77 | —(CH$_2$)$_2$—NH—(CH$_2$)$_3$—O—C$_2$H$_5$ | 0,53 |
| 78 | —CHCH$_3$—CH$_2$—NH—C(CH$_3$)$_3$ | 0,64 |
| 79 | —CHCH$_3$—CH$_2$—C(CH$_3$)$_2$—NH—CH$_3$ | 0,34 |
| 80 | —CHCH$_3$—CH$_2$—NH—(CH$_2$)$_3$—NH$_2$ | 0,10 |
| 81 | —CH$_2$—CH—COOC$_2$H$_5$<br>　　　　\|<br>　　　　NH$_2$ | 0,47 |
| 82 | —CH$_2$-(pyrrolidinyl-NH) | 0,30 |
| 83 | CH$_2$CH$_2$—N(CH$_3$)$_2$ | 0,40 |
| 84 | CH$_2$CH$_2$—N(C$_2$H$_5$)$_2$ | 0,46 |
| 85 | CH$_2$CH$_2$CH$_2$—N(CH$_3$)$_2$ | 0,37 |
| 86 | CH$_2$CH$_2$—SCH$_3$ | 0,56 |
| 87 | (tetrahydrofuryl) | 0,52 |

[+] compare Example 1

EXAMPLE 88

1-N-Ethoxycarbonyl-sisomicin 40 mg of pyrocarbonic acid diethyl ester are added to 220 mg of 2′,3,3″,6′-tetra-N-(o-nitrophenylsulphenyl)-sisomicin in 4 ml of methylene chloride and 2 ml of methanol, after 1 hour the reaction mixture is evaporated in vacuo, the protective groups are split off as described in Example 1 and the mixture is worked up. Yield: 78 mg; $R_f$ value: 0.65.

EXAMPLE 89

1-N-Ethoxycarbonyl-sisomicin

The procedure followed is analogous to Example 1, using chloroformic acid ethyl ester as the acylating agent. Yield: 20 mg; $R_f$ value: 0.65.

EXAMPLE 90

1-N-tert.-Butoxycarbonyl-sisomicin

The preparation is carried out analogously to Example 88, using pyrocarbonic acid di-(tert.-butyl) ester as the acylating agent. Yield: 75 mg; $R_f$ value: 0.79.

EXAMPLE 91

1-N-tert.-Butoxycarbonyl-sisomicin

The procedure followed is analogous to Example 1, using tert.-butoxycarbonyl azide as the acylating agent. Yield: 23 mg; $R_f$ value: 0.79.

EXAMPLE 92

1-N-(2,3-Dihydroxypropoxycarbonyl)-sisomicin 110 g of 2′,3,3″,6′-tetra-N-(o-nitrophenylsulphenyl)-sisomicin are reacted with 58 mg of 4-(2,2-diethyl-1,3-dioxolan-4-yl-methoxycarbonyloxy)-3-oxo-2,5-diphenyl-2,3-dihydrothiophene 1,1-dioxide (from Example 26a) analogously to Example 1. In order to split off the protective groups, the mixture is acidified to pH 1 and left to stand for 10–15 minutes. Thereafter, it is worked up as in Example 1. Yield: 10 mg; $R_f$ value: 0.36.

EXAMPLE 93

(a)

1-N-(p-Nitrophenoxycarbonyl)-2′,3,3″,6′-tetra-N-(o-nitro-phenylsulphenyl)-sisomicin 1.23 ml of absolute pyridine and, after 2 minutes, 1.8 g of 2′,3,3″,6′-tetra-N-(o-nitrophenylsulphenyl)-sisomicin are added to 617 mg of chloroformic acid p-nitrophenyl ester in 25 ml of absolute methylene chloride, whilst cooling with ice, and the mixture is stirred vigorously, with the exclusion of moisture. After 5 minutes, the red solution is poured onto 200 ml of ether, the precipitate is filtered off and dissolved in 40 ml of methylene chloride, the methylene chloride solution is extracted by shaking twice with 150 ml of water each time, the organic phase is concentrated to 15 ml, after drying over sodium sulphate, and the concentrate is filtered over a silica gel column (3×8 cm). After eluting the yellow zone with methylene chloride, the dark red fraction is eluted with methylene chloride/methanol (98/2) and the eluate is concentrated in vacuo. Yield: 1.2 g.

IR (KBr): 1740 (m), 1510 (s) and 1358 (s); $R_f$: (CH$_2$Cl$_2$/CH$_3$OH=97.5/2.5): 0.32

Purification by column chromatogrraphy is not necessary for subsequent reactions with amino compounds.

(b) 1-N-(Hydroxycarbamoyl)-sisomicin 0.5 ml of 1 molar aqueous-methanolic hydroxylamine solution is added to 135 mg of 1-N-(p-nitrophenoxycarbonyl)-2′,3,3″,6′-tetra-N-(o-nitrophenylsulphenyl)-sisomicin in 1.5 ml of dioxane, after 3 hours and the mixture is concentrated in vacuo, the residue is taken up in 2 ml of methylene chloride, and 3 ml of a methanolic H$_2$S solution, saturated at 0° C., and 0.2 ml of a methanolic hydrogen chloride solution, saturated at 20° C., are added. After one minute, the mixture is neutralised with concentrated ammonia solution and evaporated in vacuo, the residue is digested with 5 ml of water and the mixture is filtered. The filtrate is washed twice with ether, the aqueous phase is filtered over 5 ml of a basic ion exchanger (OH$^-$ form) and the filtrate is evaporated in vacuo. Yield: 34 mg of a colourless powder; $R_f$: 0.19.

The compounds of Table III were obtained in an analogous manner by reacting 1-N-(p-nitrophenoxy-carbonyl)-2',3,3'',6'-tetra-N-(o-nitrophenylsulphenyl)-sisomicin with the corresponding amines, hydrazines or hydroxylamines. The reactions were thereby preferably carried out with the free bases in methylene chloride, dioxane, piperidine or dimethylformamide. Salts of the amino compounds employed were treated with a suitable ion exchanger or with sodium methylate in methanol before the reaction, in order to obtain the free bases.

TABLE III.

Compounds of the formula II

| Ex. No. | A | $R_f$ value |
|---|---|---|
| 94 | $NH_2$ | 0,27 |
| 95 | $NH-CH_3$ | 0,44 |
| 96 | $N(CH_3)_2$ | 0,59 |
| 97 | (pyrrolidinyl) | 0,64 |
| 98 | $NH-CH_2-C\equiv CH$ | 0,46 |
| 99 | $NH-C(CH_3)_3$ | 0,72 |
| 100 | $NH-$(cyclohexyl) | 0,75 |
| 101 | $NH-OH$ | 0,19 |
| 102 | $NH-(CH_2)_2OH$ | 0,30 |
| 103 | $(NCH_3)-(CH_2)_2OH$ | 0,38 |
| 104 | $NH-CH_2-CH(OH)-CH_2-O-CH_2-CH=CH_2$ | 0,55 |
| 105 | $NH-CH(CH_3)-COOC_2H_5$ | 0,57 |
| 106 | $(NCH_3)-CH_2-CO-NH_2$ | 0,39 |
| 107 | $NH-(CH_2)_3CN$ | 0,52 |
| 108 | $NH-CH_2-CF_3$ | 0,56 |
| 109 | $NH-NH_2$ | 0,19 |
| 110 | $NH-N(CH_3)_2$ | 0,59 |
| 111 | $NH-(CH_2)_2-N\!\!\diagup\!\!\diagdown\!\!O$ (morpholino) | 0,51 |
| 112 | $NH-O-CH_3$ | 0,47 |
| 113 | $NH-(CH_2)_2-N(CH_3)_2$ | 0,25 |

EXAMPLE 114

1-N-(Methylcarbamoyl)-sisomicin 2 ml of a solution of 0.6 ml of methyl isocyanate in 10 ml of absolute pyridine are added to 220 mg of 2',3,3'',6'-tetra-N-(o-nitrophenylsulphenyl)-sisomicin, after 15 hours the mixture is poured onto 20 ml of ether, the precipitate is filtered off and dissolved in 3 ml of methylene chloride, and 6 ml of a methanolic $H_2S$ solution, saturated at 0° C., and 0.4 ml of a methanolic hydrogen chloride solution, saturated at 20° C., are added. After 2 minutes, the mixture is neutralised with concentrated ammonia solution and evaporated in vacuo, the residue is digested with 20 ml of water and the mixture is filtered. The filtrate is washed twice with ether and filtered over 10 ml of a basic ion exchanger ($OH^-$ form) and the eluate is evaporated in vacuo. Yield: 95 mg; $R_f$ value: 0.44.

The compounds listed in Table IV are prepared in this manner, using the corresponding isocyanates.

TABLE IV

Compounds of the formula II

| Example No. | A | $R_f$ value++ |
|---|---|---|
| 115 | $CH_3-O-CH_2NH$ | 0,46 |
| 116 | $C_2H_5-O-CH_2NH$ | 0,41 |
| 117 | $CH_3-(CH_2)_5-O-CH_2NH$ | 0,42 |
| 118 | $CH_3O-CONH$ | 0,45 |
| 119 | $C_2H_5O-CONH$ | 0,45 |

++see Example 1

EXAMPLE 120

1-N-(Phenoxycarbonyl-carbamoyl)-2',3,3'',6'-tetra-N-(o-nitrophenylsulphenyl)-sisomicin 0.41 ml of a solution of 0.15 ml of phenoxycarbonyl isocyanate in 0.85 ml of methylene chloride is added dropwise to 440 mg of 2',3,3'',6'-tetra-N-(o-nitrophenylsulphenyl)-sisomicin in 4 ml of absolute methylene chloride, after 2 minutes the mixture is poured onto 50 ml of ether and the precipitate is filtered off and dried. Yield: 405 mg. IR (KBr): 1740 (m), 1700 (m) and 1510 (s); $R_f$ ($CH_2Cl_2/CH_3OH=95/5$): 0.95.

EXAMPLE 121

1-N-(Allophanyl)-sisomicin

A few drops of concentrated ammonia are added to 120 mg of 1-N-(phenoxycarbonyl-carbamoyl)-2',3,3'',6'-tetra-N-(o-nitrophenylsulphenyl)sisomicin in 2 ml of methylene chloride and 1 ml of methanol and the solution is worked up as described under Example 114. Yield: 40 mg; $R_f$ value 0.36.

EXAMPLE 122

1-N-(4-Hydroxyethylallophanyl)-sisomicin

The preparation is carried out with ethanolamine, and otherwise as described in Example 121. Yield: 35 mg; $R_f$ value: 0.43.

EXAMPLE 123

1-N-(N-Methyl-N-morpholinocarbonyl-carbamoyl)-sisomicin 110 mg of 2',3,3'',6'-tetra-N-(o-nitrophenylsulphenyl)-sisomicin and 40 mg of N-methyl-N-morpholinocarbonyl-(2-chloro-4-nitro-phenyl)-urethane are left in 0.5 ml of absolute pyridine at room temperature for 24 hours, the mixture is evaporated in vacuo and splitting off of the protective groups and working up are carried out as in Example 114. Yield: 38 mg; $R_f$ value: 0.62.

EXAMPLE 124

1-N-(2-Hydroxyethoxycarbonyl)sisomicin 165 mg of 2',3,3'',6'-tetra-N-(o-nitrophenylsulphenyl)-sisomicin are reacted with 84 mg of 4-nitrophenyl 2-triphenylmethoxyethyl carbonate analogously to Example 1. In order to additionally split off the trityl radical, which can be followed by thin layer chromatography, the solution containing hydrochloric acid is left to stand at room temperature for 15 minutes, diluted with water and then worked up as in Example 1. Yield: 25 mg. $R_f$ value: 0.43.

EXAMPLE 125

1-N-(1,3-Dihydroxyprop-2-oxycarbonyl)-sisomicin

The procedure is analogous to Example 92, using the intermediate product from Example 39a. $R_f$ value: 0.32.

EXAMPLE 126

1-N-(2,2-Bis-hydroxymethyl-butoxycarbonyl)-sisomicin

The procedure is analogous to Example 92, using the intermediate product from Example 37a. $R_f$ value: 0.50.

EXAMPLE 127

1-N-(D-Glucopyranosyl-3-carbonyl)-sisomicin 35 mg of the product from Example 29 are dissolved in a little dilute hydrochloric acid and, in order to split off the isopropylidene groups, the solution is left to stand at room temperature for 2 hours, treated with a basic ion exchanger and evaporated. Yield: 22 mg. $R_f$ value: 0.48.

Among the new salts of the invention, those salts that are pharmaceutically acceptable are particularly important and are preferred.

The new free compounds of the general formula I and their salts can be interconverted in any suitable manner; methods for such interconversion are known in the art.

The present invention also comprises pharmaceutically acceptable bioprecursors of the active compounds of the present invention.

For the purposes of this specification the term 'pharmaceutically acceptable bioprecursor' of an active compound of the invention means a compound having a structural formula different from the active compound but which nonetheless, upon administration to a warm-blooded animal is converted in the animal's body to the active compound.

We claim:

1. A compound of the formula

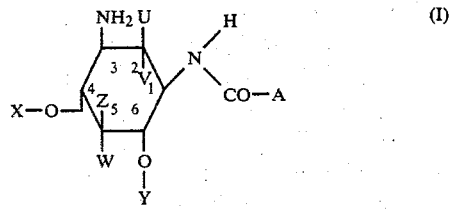

or a pharmaceutically acceptable salt thereof, in which

X denotes a radical of the formula

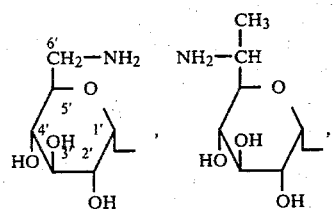

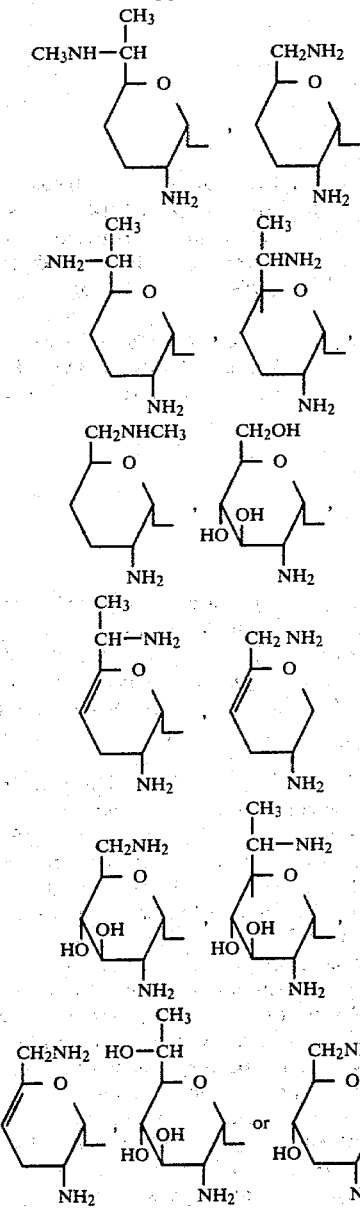

Y denotes a radical of the formula

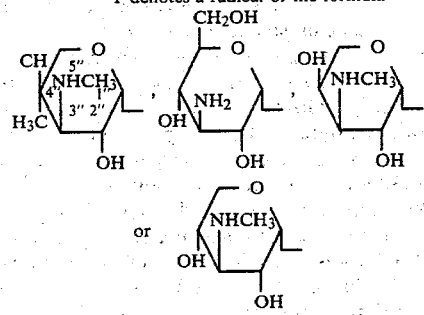

U, V, and W independently denote a hydrogen atom or a hydroxyl group, but U and V cannot be OH simultaneously Z denotes a hydrogen atom or a hydroxyl or amino group, and A denotes a radical

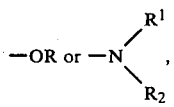

in which
R denotes an alkyl radical with 1 to 10 carbon atoms, which is unsubstituted or substituted by 1 or 2 substituents selected from halogen; hydroxyl; mercapto; cyano; carboxyl. trifluoromethyl; alkoxy and alkylthio with 1 to 6 carbon atoms; allyloxy; phenoxy; alkoxycarbonyl with 1 to 4 carbon atoms in the alkyl radical and cycloalkyl with 3 to 6 carbon atoms in the ring; and a radical of the general formula

in which
$R_6$ denotes a hydrogen atom, a $C_1$ to $C_8$ alkyl group or an allyl group and
$R_7$ denotes a hydrogen or a $C_1$ to $C_8$ alkyl, $C_5$ to $C_7$ cycloalkyl, $C_5$ to $C_7$ cycloalkyl-$C_1$ to $C_4$ alkyl, phenyl, phenyl-$C_1$ to $C_4$ alkyl or allyl group, and
in which
the alkyl, cycloalkyl and phenyl radicals $R_6$ and $R_7$ are unsubstituted or substituted by one or two substituents selected from alkoxy with 1 to 4 carbon atoms, amino, monoalkylamino and dialkylamino with 1 to 4 carbon atoms per alkyl group in each case and hydroxyl; or R denotes an alkenyl radical with 3 to 7 carbon atoms; or denotes an alkinyl radical with 3 or 4 carbon atoms; or denotes a monocyclic or bicyclic cycloalkyl radical with 3 to 7 carbon atoms, which is unsubstituted or contains 1, 2 or 3 substituents selected from alkyl with 1 to 4 carbon atoms, alkoxy with 1 to 4 carbon atoms, hydroxyl, amino and alkylamino and dialkylamino with 1 to 4 carbon atoms per alkyl group, or denotes a phenyl radical or benzyl radical, which is unsubstituted or substituted by nitro, halogen or alkoxy with 1 to 4 carbon atoms; or denotes a piperidinyl, tetrahydropyranyl, tetrahydrofuryl, 1,3-dioxolanyl or 1,3-dioxolano[d,b]tetrahydrofuryl radical, which is unsubstituted or substituted by 1 or 2 radicals selected from alkoxy with 1 to 4 carbon atoms, hydroxyl, alkyl with 1 to 4 carbon atoms and 2,2-dimethyl-1,3-dioxolan-4-yl; or denotes a 1,3-dioxolanylalkyl, tetrahydrofurylalkyl, tetrahydropyranylalkyl, oxetanylalkyl, 1,3-oxathiolanylalkyl, 1,3-dithiolanylalkyl, 1,4-dioxaspiro[4,5]decanyl, alkyl, oxiranylalkyl, piperidinylalkyl, tetrahydropyridinylalkyl or aziridinylalkyl radical in which the alkyl radical contains 1 to 4 carbon atoms and which is unsubstituted or carries 1 or 2 substituents selected from alkyl with 1 to 4 carbon atoms, phenyl and alkoxy with 1 to 4 carbon atoms, and
$R^1$, independently of R, has any of the meanings indicated for R or denotes a hydrogen atom; and
$R^2$ independently of R has any of the meanings given for R or denotes a hydrogen atom or a 1-B-tetra-O-ocetyl-D-glucosyl, 1-B-D-glucosyl, tetrahydropyridinyl, morpholino, piperidino, alkoxy with 1 to 4 carbon atoms, cyclopentyloxy, cyclohexyloxy, benzyloxy which is optionally substituted by halogen, tetrahydropyranyloxy, tetrahydrofuranyloxy, hydroxyl, amino, alkylamino and dialkylamino with 1 to 4 carbon atoms per alkyl group, alkoxycarbonyl with 1 to 4 carbon atoms in the alkyl radical, or allyloxycarbonyl group or a group of the formula

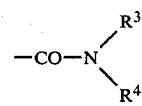

in which
$R^3$ independently of $R^1$ has any of the meanings given for $R^1$, and
$R^4$ denotes a hydrogen atom, an alkyl radical with 1 to 10, carbon atoms, which optionally carries 1 or 2 substituents selected from halogen, hydroxyl, mercapto, cyano, trifluoromethyl, alkoxy with 1 to 6 carbon atoms, allyloxy, phenoxy, amino, alkylamino and dialkylamino with 1 to 4 carbon atoms per alkyl group, the alkylamino groups mentioned being unsubstituted or substituted by —OH, alkoxycarbonyl with 1 to 4 carbon atoms in the alkyl radical and cycloalkyl with 3 to 6 carbon atoms in the ring, or denotes a monocyclic or bicyclic cycloalkyl radical with 3 to 7 carbon atoms, which can contain 1, 2 or 3 substituents selected from alkyl with 1 to 4 carbon atoms, alkoxy with 1 to 4 carbon atoms, hydroxyl, amino or alkylamino or dialkylamino with 1 to 4 carbon atoms per alkyl group; or denotes a hydroxyl, alkoxy with 1 to 4 carbon atoms, or amino group or an alkylamino or dialkylamino group with 1 to 4 carbon atoms per alkyl group,
or $R^1$ and $R^2$ or $R^3$ and $R^4$, including the N atom to which they are bonded, form a pyrrolidino, piperidino, morpholino, piperazin-4-yl, hexamethyleneimino, isoxazolin-2-yl or tetrahydroisoxazin-2-yl ring, which optionally carries 1 or 2 alkyl groups with 1 to 4 carbon atoms, which can be substituted by hydroxyl.

2. A compound according to claim 1 which is derived from an antibiotic selected from gentamicin A, gentamicin B, gentamicin $B_1$, gentamicin $C_1$, gentamicin $C_{1a}$, gentamicin $C_2$, gentamicin $C_{2a}$, gentamicin $C_{2b}$, gentamicin $X_2$, sisomicin, verdamicin, tobramicin, G-418, 66-40D, JI-20A, JI-20B, G 52 mutamicin 1, mutamicin 2, mutamicin 4, mutamicin 5 and mutamicin 6, and which carries the radical —CO—A wherein A is defined as in claim 31 on the 1-N atom of the antibiotic.

3. A compound according to claim 1 of the formula

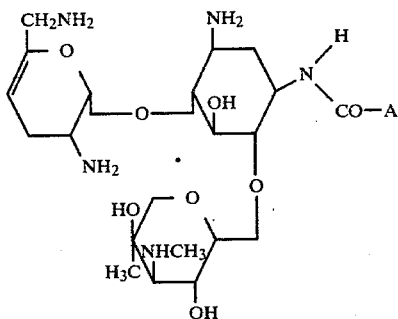

(II)

in which A has the same meaning as in claim 1.

4. A compound according to claim 1, in which R denotes an alkyl radical with 1 to 6 carbon atoms unsubstituted or substituted by 1 or 2 substituents selected from chlorine, methoxy or ethoxy which is unsubstituted or substituted in the alkyl part by amino, or monoalkylamino or dialkylamino with 1 to 4 carbon atoms per alkyl group in each case, or R denotes an allyl or propargyl radical; a monocyclic or bicyclic cycloalkyl radical with 3 to 7 carbon atoms, which is unsubstituted or contains 1, 2 or 3 substituents selected from methyl, ethyl, methoxy ethoxy, methylamino and dimenthylamino; a phenyl radical or a benzyl radical, which is unsubstituted or substituted by chlorine, a piperidinyl, tetrahydropyranyl, tetrahydrofuryl, 1,3-dioxolanyl or 1,3-dioxolano[d,b]tetrahydrofuryl radical which is unsubstituted or substituted by 1 or 2 radicals selected from methoxy, ethoxy, methyl and ethyl; a 1,3-dioxolanylalkyl, tetrahydrofurylalkyl, tetrahydropyranylalkyl, oxetanylalkyl, 1,3-oxathiolanylalkyl, 1,3-dithiolanylalkyl, 1,4-dioxaspiro[4,5]decanyl, oxiranylalkyl, piperidinylalkyl, tetrahydropyridinylalkyl or aziridinylalkyl radical in which the alkyl radical contains 1 or 2 carbon atoms and is unsubstituted or substituted by 1 or 2 substituents selected from methyl, ethyl, phenyl, methoxy and ethoxy, $R^2$ denotes a benzyloxy group which is unsubstituted or substituted by chlorine, methylamino, or ethylamino or a methoxycarbonyl or ethoxycarbonyl group or a group of the general formula $$-CO-N\begin{matrix}R^3\\R^4\end{matrix}$$

in which $R^3$ has the same meaning as in claim 1 and $R^4$ denotes an alkyl radical with 1 to 6 carbon atoms which is unsubstituted or substituted by 1 or 2 substituents selected from chlorine, methoxy, ethoxy, methylamino and dimethylamino unsubstituted or substituted by cycloalkylmethyl or cycloalkylethyl, or denotes a monocyclic or bicyclic cycloalkyl radical with 3 to 7 carbon atoms which is unsubstituted or substituted by 1, 2 or 3 substituents selected from methyl, ethyl, methoxy, ethoxy, methylamino and dimethylamine, or denotes a methoxy, ethoxy, methylamine or ethylamino group.

5. A compound of claim 1 which is a 1-N-Carbamoyl-sisomicin or a salt thereof.

6. A compound of claim 1 which is a 1-N-(Methylcarbamoyl)-sisomicin or a salt thereof.

7. A compound of claim 1 which is a 1-N-Methoxymethylcarbamoyl)-sisomicin or a salt thereof.

8. A compound of claim 1 which is a 1-N-(Hydroxycarbamoyl)-sisomicin or a salt thereof.

9. A compound of claim 1 which is a 1-N-(2-Aminoethylcarbamoyl)-sisomicin or a salt thereof.

10. A compound of claim 1 which is a 1-N-(2-Aminoethoxycarbonyl)-sisomicin or a salt thereof.

11. A compound of claim 1 which is a 1-N-(Methyl-2-amino-ethoxycarbonyl)-sisomicin or a salt thereof.

12. A compound of claim 1 which is a 1-N-(3-Aminopropoxycarbonyl)-sisomicin or a salt thereof.

13. A compound of claim 1 which is a 1-N-(2,3-Dihydroxypropoxycarbonyl)-sisomicin or a salt thereof.

14. A compound according to claim 1, in which the radical

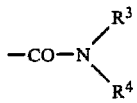

denotes an amino group, an alkylamino or dialkylamino group with 1 to 4 carbon atoms per alkyl group in each case, the $C_1$ to $C_4$ alkyl radicals present in the alkylamino and dialkylamino substituents being unsubstituted or further substituted by one or two substituents selected from alkoxy with 1 to 4 carbon atoms, amino, monoalkylamino and dialkylamino with 1 to 4 carbon atoms per alkyl group in each case and hydroxyl, an allyl amino group or a diallylamino group.

15. A pharmaceutical composition containing as an active ingredient an antimicrobially effective amount of a compound according to claim 1 in admixture with a solid or liquefied gaseous diluent or in admixture with a liquid diluent other than a solvent of a molecular weight less than 200 except in the presence of a surface- active agent.

16. A pharmaceutical composition containing as an active ingredient an antimicrobially effective amount of a compound according to claim 1 in the form of a sterile or physiologically isotonic aqueous solution.

17. A medicament in dosage until form comprising an antimicrobially effective amount of a compound according to claim 1 and an inert pharmaceutical carrier.

18. A medicament of claim 17 in the form of tablets, pills, dragees, capsules, ampoules, or suppositories.

19. A method of combating bacterial infections in warm-blooded animals which comprises administering to the animals an antimicrobially effective amount of an active compound according to claim 1 either alone or in admixture with a diluent or in the form of a medicament.

20. A method according to claim 19 in which the active compound is administered to a warm-blooded animal in an amount of 20 mg/day to 2,000 mg/day.

21. A method according to claim 20 in which the active compound is administered to a warm-blooded animal in an amount of 100 to 500 mg/day.

22. A method according to claim 19 in which the animal is a ruminant.

23. A method according to claim 19 in which the active compound is administered orally.

* * * * *

UNITED STATES PATENT AND TRADEMARK OFFICE
CERTIFICATE OF CORRECTION

PATENT NO. : 4,234,572

DATED : November 18, 1980

INVENTOR(S) : Uwe Petersen, et al.

It is certified that error appears in the above—identified patent and that said Letters Patent is hereby corrected as shown below:

Column 1, line 19, "aminoglycose" should be --aminoglycoside--.
Column 3, line 16, "pharmaceuticaly" should be --pharmaceutically--.
Column 7, line 45 delete "b" from "4".
Column 26, line 47, "bloodios-" should be --bloodiso- --.
Column 42, line 50, "chromatogrraphy" should be --chromatography--.
Column 48, line 66, "31" should be --1--.

Signed and Sealed this

Seventh Day of April 1981

[SEAL]

Attest:

RENE D. TEGTMEYER

Attesting Officer   Acting Commissioner of Patents and Trademarks